US009018354B2

(12) United States Patent
Kase et al.

(10) Patent No.: US 9,018,354 B2
(45) Date of Patent: Apr. 28, 2015

(54) METHODS OF PRODUCING PROTEINS HAVING TRIPLE-HELIX STRUCTURE

(75) Inventors: Tetsuo Kase, Osaka (JP); Akio Kimura, Osaka (JP); Hiroshi Kisaki, Osaka (JP); Yoko Kisaki, legal representative, Isa (JP); Hiroyuki Keshi, Osaka (JP); Aya Keshi, legal representative, Osaka (JP); Hiroshi Ueyama, Osaka (JP); Mizuki Nishihara, Osaka (JP)

(73) Assignees: Fuso Pharmaceutical Industries, Ltd., Osaka (JP); Osaka Prefectural Government, Osaka (JP)

( * ) Notice: Subject to any disclaimer, the term of this patent is extended or adjusted under 35 U.S.C. 154(b) by 1795 days.

(21) Appl. No.: 11/909,873

(22) PCT Filed: Mar. 31, 2006

(86) PCT No.: PCT/JP2006/306941
§ 371 (c)(1),
(2), (4) Date: Aug. 26, 2011

(87) PCT Pub. No.: WO2006/106970
PCT Pub. Date: Oct. 12, 2006

(65) Prior Publication Data
US 2012/0172577 A1 Jul. 5, 2012

(30) Foreign Application Priority Data
Mar. 31, 2005 (JP) ................................. 2005-102999

(51) Int. Cl.
A61K 38/39 (2006.01)
C12P 21/02 (2006.01)
C07K 14/78 (2006.01)

(52) U.S. Cl.
CPC *C12P 21/02* (2013.01); *C07K 14/78* (2013.01)

(58) Field of Classification Search
None
See application file for complete search history.

(56) References Cited

U.S. PATENT DOCUMENTS

| 5,405,757 A | 4/1995 | Prockop et al. |
| 5,593,859 A | 1/1997 | Prockop et al. |
| 2002/0098578 A1* | 7/2002 | Prockop et al. ............... 435/325 |
| 2002/0142391 A1* | 10/2002 | Kivirikko et al. ............ 435/69.1 |

FOREIGN PATENT DOCUMENTS

| JP | 7-501939 | 3/1995 |
| JP | 10-179169 | 7/1998 |
| JP | 2000-508544 | 7/2000 |
| JP | 3302017 | 4/2002 |
| JP | 2004-16144 | 1/2004 |
| WO | 93/07889 | 4/1993 |
| WO | 97/38710 | 10/1997 |

OTHER PUBLICATIONS

English Machine Translation JP-H10-176169; 1998.*
Nokelainen et al., "High-level production of human type I collagen in the yeast *Pichia pastoris*", Yeast 2001; 18: 797-806. DOI: 10.1002/yea.730.*
Ala-Kokko et al., "Human mRNA for pro-alpha-1 type 3 collagen" GenBank, X14220. 1 (Mar. 31. 1995).
Fertala et al., "Synthesis of recombinant human procollagen II in a stably transfected tumour cell line (HT1080)" Biochem J. (Feb. 15, 1994) 298 (Pt. 1):31-7.
Gotkin et al., "*Homo sapiens* collagen, type 1, alpha 2 (COL1A2), mRNA" NCBI Reference Sequence: NM_000089. 3 (Dec. 20, 2004).
Long et al., "*Homo sapiens* collagen, type 1, alpha 1 (COL1A1), mRNA" NCBI Reference Sequence: NM_000088. 3 (Dec. 20, 2004).
Mieno et al., "*Homo sapiens* collagen, type II, alpha 1 (primary osteoarthritis, spondyloepiphyseal dysplasia, congenital) (COL2A1), transcript variant 1, mRNA", NCBI Reference Sequence: NM_001844. 3 (Oct. 26, 2004).
John et al., "Expression of an engineered form of recombinant procollagen in mouse milk" Nat Biotechnol. (Apr. 1999) 17(4):385-9.
Lamberg et al., "Characterized of Human Type III Collagen Expressed in a Baculovirus System" J Biol Chem. (May 17, 1996) 271(20):11988-95.
Myllyharju et al., "Expression of recombinant human type I-III collagens in the yeast *Pichia pastoris*" Biochem Soc Trans. (2000) 28(4):353-7.
Ala-Kokko et al., "Expression of a Human Cartilage Procollagen Gene (COL2A1) in Mouse 3T3 Cells" J. Biol. Chem. 266(22):14175-8 (Aug. 5, 1991).
Bignall et al., "Collagen treatment in rheumatoid arthritis" Lancet, 342(8874):799 (Sep. 25, 1993).
Bulleid et al., "Recombinant expression systems for the production of collagen" Biochem. Soc. Trans., 28(4):350-3 (2000).

(Continued)

Primary Examiner — Suzanne M Noakes
(74) Attorney, Agent, or Firm — Karl Bozicevic; Bozicevic, Field & Francis LLP

(57) ABSTRACT

An objective of the present invention is to provide methods of producing human collagen molecules that are easy to isolate and purify and that have a structure substantially equivalent to that of a natural collagen molecule, wherein host cells that are transduced with a collagen gene synthesize large amounts of human collagen protein derived from a gene introduced into a high exogenous gene expression vector. Another objective of the present invention is to provide collagen molecules produced by the production methods.

The present inventors discovered that a large amount of human collagen hardly contaminated with host cell-derived collagen could be produced, by selecting from various mammalian cells a host cell that has low collagen expression and introducing a collagen gene construct into a vector capable of high exogenous gene expression.

11 Claims, 14 Drawing Sheets

(56) References Cited

OTHER PUBLICATIONS

Frischholz et al., "Characterization of Human Type X Procollagen and Its NC-1 Domain Expressed as Recombinant Proteins in HEK293 Cells" J. Biol. Chem., 273(8):4547-55 (Feb. 20, 1998).

Fukuda et al., "Formation of Recombinant Triple-Helical (a1(IV)2a2(IV) Collagen Molecules in CHO Cells" Biochem. Biophys. Res. Commun., 231(1):178-82 (Feb. 3, 1997).

Imamura et al., "Bone Morphogenetic Protein-1 Processes the NH2-terminal Propeptide, and a Furin-like Proprotein Convertase Processes the COOH-terminal Propeptide of pro-a1(V) Collagen" J. Biol. Chem., 273(42):27511-7 (Oct. 16, 1998).

Peacock et al., "The Effect of Hydroxyproline and Reconstituted Collagen Upon Wound Healing in Protein Depleted Rats" Surg. Forum., 10:303-7 (1960).

Shoshan et al., "Acceleration of Wound Healing Induced by Enriched Collagen Solutions" J. Surg. Res., 10 (10):485-91 (Oct. 1970).

Stacey et al., "Rescue of Type I Collagen-Deficient Phenotype by Retroviral-Vector-Mediated Transfer of Human proa1(I) Collagen Gene into Mov-13 Cells" J. Virol., 61(8):2549-54 (Aug. 1987).

Trentham et al., "Effects of Oral Administration of Type II Collagen on Rheumatoid Arthritis" Science, 261 (5129):1727-30 (Sep. 24, 1993).

Fukui et al, Processing of Type II Procollagen Amino Propeptide by Matrix Metalloproteinases. J. Biol. Chem 277 (3): 2193-201; Jan. 18, 2002.

Berlec et al., "Current state and recent advances in biopharmaceutical production in *Escherichia coli*, yeasts and mammalian cells" J. Ind. Microbiol. Biotechnol. (2013) 40:257-274.

Olsen et al., "Recombinant collagen and gelatin for drug delivery" Advanced Drug Delivery Reviews (2003) 55:1547-1567.

Terajima et al., "Glycosylation and Cross-Linking in Bone Type I Collagen" The Journal of Biological Chemistry (2014) 289:22636-22647.

* cited by examiner

SEQUENCE LISTING

```
<160> NUMBER OF SEQ ID NOS: 12

<210> SEQ ID NO 1
<211> LENGTH: 4395
<212> TYPE: DNA
<213> ORGANISM: Homo sapiens

<400> SEQUENCE: 1
atgttcagct ttgtggacct ccggctcctg ctcctcttag cggccaccgc cctcctgacg      60
cacggccaag aggaaggcca agtcgagggc caagacgaag acatcccacc aatcacctgc     120
gtacagaacg gcctcaggta ccatgaccga gacgtgtgga aacccgagcc ctgccggatc     180
tgcgtctgcg acaacggcaa ggtgttgtgc gatgacgtga tctgtgacga gaccaagaac     240
tgccccggcg ccgaagtccc cgaggcgag tgctgtcccg tctgccccga cggctcagag     300
tcacccaccg accaagaaac caccggcgtc gagggaccca agggagacac tggccccga     360
```

```
ggcccaaggg gacccgcagg ccccccctggc cgagatggca tccctggaca gcctggactt    420
cccggacccc ccggacccc  cggacctccc ggaccccctg gcctcggagg aaactttgct    480
ccccagctgt cttatggcta tgatgagaaa tcaaccggag gaatttccgt gcctggcccc    540
atgggtccct ccggtcctcg tggtctccct ggccccctg  gtgcacctgg tccccaaggc    600
ttccaaggtc ccctggtga  gcctggcgag cctggagctt caggtcccat gggtccccga    660
ggtcccccag gtcccctgg  aaagaatgga gatgatgggg aagctggaaa acctggtcgt    720
cctggtgagc gtgggcctcc tgggcctcag ggtgcccgag gattgcccgg aacagctggc    780
ctccctggaa tgaagggaca cagaggtttc agtggtttgg atggtgccaa gggagatgct    840
ggtcctgctg gtcctaaggg tgagcctggc agccctggtg aaaatggagc tcctggtcag    900
atgggccccc gtggcctgcc tggtgagaga ggtcgccctg gagcccctgg ccctgctggt    960
gctcgtggaa atgatggtgc tactggtgct gccgggcccc ctggtcccac cggccccgct   1020
ggtcctcctg gcttccctgg tgctgttggt gctaagggtg aagctggtcc ccaagggccc   1080
cgaggctctg aaggtcccca gggtgtgcgt ggtgagcctg gccccctgg  ccctgctggt   1140
gctgctggcc ctgctggaaa ccctggtgct gatggacagc ctggtgctaa aggtgccaat   1200
ggtgctcctg gtattgctgg tgctcctggc ttccctggtg cccgaggccc ctctggaccc   1260
cagggccccg cgcccctcc  tggtcccaag ggtaacagcg gagaacctgg tgctcctggc   1320
agcaaaggag acactggtgc taaggagag  cctggccctg ttggtgttca aggaccccct   1380
ggccctgctg gagaggaagg aaagcgagga gctcgaggtg aacccggacc cactggcctg   1440
cccggacccc ctggcgagcg tggtggacct ggtagccgtg gtttccctgg cgcagatggt   1500
gttgctggtc caagggtcc  cgctggtgaa cgtggttctc ctggccctgc tggccccaaa   1560
ggatctcctg gtgaagctgg tcgtccggt  gaagctggtc tgcctggtgc aagggtctg    1620
actgaagcc  ctggcagccc tggtcctgat ggcaaaactg gcccccctgg tcccgccggt   1680
caagatggtc gccccggacc cccaggccca cctggtgccc gtggtcaggc tggtgtgatg   1740
ggattccctg gacctaaagg tgctgctgga gagcccggca aggctggaga gcgaggtgtt   1800
cccgacccc  ctggcgctgt cggtcctgct ggcaaagatg gagaggctgg agctcaggga   1860
ccccctggcc ctgctggtcc cgctggcgag agaggtgaac aaggccctgc tggctcccc    1920
ggattccagg gtctccctgg tcctgctggt cctccaggtg aagcaggcaa acctggtgaa   1980
cagggtgttc ctggagacct tggcgccct  ggcccctctg gagcaagagg cgagagaggt   2040
ttccctggcg agcgtggtgt gcaaggtccc cctggtcctg ctggtccccg aggggccaac   2100
ggtgctcccg gcaacgatgg tgctaagggt gatgctggtg cccctggagc tcccggtagc   2160
cagggcgccc ctggccttca gggaatgcct ggtgaacgtg gtgcagctgg tcttccaggg   2220
cctaagggtg acagaggtga tgctggtccc aaaggtgctg atggctctcc tggcaaagat   2280
ggcgtccgtg gtctgaccgg ccccattggt cctcctggcc ctgctggtgc cctggtgac    2340
aagggtgaaa gtggtcccag cggccctgct ggtcccactg gagctcgtgg tgccccgga    2400
gaccgtggtg agcctggtcc cccggccct  gctggctttg ctggccccc  tggtgctgac   2460
ggccaacctg tgctaaagg  cgaacctggt gatgctggtg ctaaaggcga tgctggtccc   2520
cctggccctg ccggacccgc tggaccccct ggccccattg gtaatgttgg tgctcctgga   2580
gccaaaggtg ctcgcggcag cgctggtccc cctggtgcta ctggtttccc tggtgctgct   2640
ggccgagtcg gtcctcctgg cccctctgga aatgctggac cccctggccc tcctggtcct   2700
```

```
gctggcaaag aaggcggcaa aggtccccgt ggtgagactg gccctgctgg acgtcctggt    2760
gaagttggtc ccctggtcc ccctggccct gctggcgaga aaggatcccc tggtgctgat    2820
ggtcctgctg gtgctcctgg tactcccggg cctcaaggta ttgctggaca gcgtggtgtg    2880
gtcggcctgc ctggtcagag aggagagaga ggcttccctg gtcttcctgg ccctctggt    2940
gaacctggca acaaggtcc ctctggagca agtggtgaac gtggtccccc tggtcccatg    3000
ggccccctg gattggctgg acccctggt gaatctggac gtgaggggc tcctggtgcc     3060
gaaggttccc ctggacgaga cggttctcct ggcgccaagg gtgaccgtgg tgagaccggc    3120
cccgctggac cccctggtgc tcctggtgct cctggtgccc ctggcccgt ggccctgct     3180
ggcaagagtg gtgatcgtgg tgagactggt cctgctggtc ccgccggtcc tgtcggccct    3240
gttggcgccc gtggccccgc cggaccccaa ggccccgtg gtgacaaggg tgagacaggc    3300
gaacagggcg acagaggcat aaagggtcac cgtggcttct ctggcctcca gggtccccct    3360
ggccctcctg gctctcctgg tgaacaaggt ccctctggag cctctggtcc tgctggtccc    3420
cgaggtcccc ctggctctgc tggtgctcct ggcaaagatg gactcaacgg tctccctggc    3480
cccattgggc ccctggtcc tcgcggtcgc actggtgatg ctggtcctgt tggtcccccc    3540
ggccctcctg gacctcctgg tccccctggt cctcccagcg ctggtttcga cttcagcttc    3600
ctgccccagc cacctcaaga gaaggctcac gatggtggcc gctactaccg ggctgatgat    3660
gccaatgtgg ttcgtgaccg tgacctcgag gtggacacca ccctcaagag cctgagccag    3720
cagatcgaga acatccggag cccagagggc agccgcaaga accccgcccg cacctgccgt    3780
gacctcaaga tgtgccactc tgactggaag agtggagagt actggattga ccccaaccaa    3840
ggctgcaacc tggatgccat caaagtcttc tgcaacatgg agactggtga gacctgcgtg    3900
taccccactc agcccagtgt ggcccagaag aactggtaca tcagcaagaa ccccaaggac    3960
aagaggcatg tctggttcgg cgagagcatg accgatggat tccagttcga gtatggcggc    4020
cagggctccg accctgccga tgtggccatc cagctgacct tcctgcgcct gatgtccacc    4080
gaggcctccc agaacatcac ctaccactgc aagaacagcg tggcctacat ggaccagcag    4140
actggcaacc tcaagaaggc cctgctcctc cagggctcca acgagatcga gatccgcgcc    4200
gagggcaaca gccgcttcac ctacagcgtc actgtcgatg gctgcacgag tcacaccgga    4260
gcctggggca agacagtgat tgaatacaaa accaccaaga cctcccgcct gcccatcatc    4320
gatgtggccc ccttggacgt tggtgcccca gaccaggaat tcggcttcga cgttggccct    4380
gtctgcttcc tgtaa                                                    4395

<210> SEQ ID NO 2
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 2
gcggccgcca ccatgttcag ctttgtggac ctccg                               35

<210> SEQ ID NO 3
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 3
```
ttctagatta caggaagcag acagggccaa                                               30

<210> SEQ ID NO 4
<211> LENGTH: 4101
<212> TYPE: DNA
<213> ORGANISM: Homo sapiens

<400> SEQUENCE: 4

| | |
|---|---|
| atgctcagct tgtggatac gcggactttg ttgctgcttg cagtaacctt atgcctagca | 60 |
| acatgccaat ctttacaaga ggaaactgta agaaagggcc cagccggaga tagaggacca | 120 |
| cgtggagaaa gggtccacc aggcccccca ggcagagatg gtgaagatgg tcccacaggc | 180 |
| cctcctggtc cacctggtcc tcctggcccc ctggtctcg gtgggaactt tgctgctcag | 240 |
| tatgatggaa aaggagttgg acttggccct ggaccaatgg gcttaatggg acctagaggc | 300 |
| ccacctggtg cagctggagc cccaggccct caaggtttcc aaggacctgc tggtgagcct | 360 |
| ggtgaacctg gtcaaactgg tcctgcaggt gctcgtggtc cagctggccc tcctggcaag | 420 |
| gctggtgaag atggtcaccc tggaaaaccc ggacgacctg gtgagagagg agttgttgga | 480 |
| ccacagggtc tcgtggtttt ccctggaact cctggacttc ctggcttcaa aggcattagg | 540 |
| ggacacaatg gtctggatgg actgaaggga cagcccggtg ctcctggtgt gaagggtgaa | 600 |
| cctggtgccc ctggtgaaaa tggaactcca ggtcaaacag agcccgtgg gcttcctggc | 660 |
| gagagaggac gtgttggtgc ccctggccca gctggtgccc gtgcagtga tggaagtgtg | 720 |
| ggtcccgtgg gtcctgctgg tcccattggg tctgctggcc ctccaggctt ccaggtgcc | 780 |
| cctggcccca agggtgaaat tggagctgtt ggtaacgctg gtcctgctgg tcccgccggt | 840 |
| ccccgtggtg aagtgggtct tccaggcctc tccggccccg ttggacctcc tggtaatcct | 900 |
| ggagcaaacg gccttactgg tgccaaggt gctgctggcc ttcccggcgt tgctggggct | 960 |
| cccggcctcc ctggacccg cggtattcct ggcctgttg gtgctgccgg tgctactggt | 1020 |
| gccagaggac ttgttggtga gcctggtcca gctggctcca aggagagag cggtaacaag | 1080 |
| ggtgagcccg ctctgctgg gccccaaggt cctcctggtc ccagtggtga agaaggaaag | 1140 |
| agaggcccta tggggaagc tggatctgcc ggccctccag gacctcctgg gctgagaggt | 1200 |
| agtcctggtt ctcgtggcct tctggagct gatggcagag ctggcgtcat gggccctcct | 1260 |
| ggtagtcgtg gtgcaagtgg ccctgctgga gtccgaggac ctaatggaga tgctggtcgc | 1320 |
| cctggggagc ctggtctcat ggacccaga ggtcttcctg gttcccctgg aaatatcggc | 1380 |
| cccgctggaa agaaggtcc tgtcggcctc cctggcatcg acggcaggcc tggcccaatt | 1440 |
| ggccccgctg gagcaagagg agagcctggc aacattggat ccctggacc caaaggcccc | 1500 |
| actggtgatc ctggcaaaaa cggtgataaa ggtcatgctg gtcttgctgg tgctcggggt | 1560 |
| gctccaggtc ctgatggaaa caatggtgct cagggacctc tggaccaca gggtgttcaa | 1620 |
| ggtggaaaag gtgaacaggg tcccgctggt cctccaggct ccagggtct gcctggcccc | 1680 |
| tcaggtcccg ctggtgaagt tggcaaacca ggagaaaggg gcctccatgg tgagtttggt | 1740 |
| ctccctggtc ctgctggtcc aagaggggaa cgcggtcccc aggtgagag tggtgctgcc | 1800 |
| ggtcctactg gtcctattgg aagccgaggt ccttctggac cccagggcc tgatggaaac | 1860 |
| aagggtgaac ctggtgtggt tggtgctgtg ggcactgctg gtccatctgg tcctagtgga | 1920 |
| ctcccaggag agaggggtgc tgctggcata cctggaggca aggagaaaa gggtgaacct | 1980 |
| ggtctcagag gtgaaattgg taaccctggc agagatggtg ctcgtggtgc cctggtgct | 2040 |

```
gtaggtgccc ctggtcctgc tggagccaca ggtgaccggg gcgaagctgg ggctgctggt    2100
cctgctggtc ctgctggtcc tcggggaagc cctggtgaac gtggtgaggt cggtcctgct    2160
ggccccaatg gatttgctgg tcctgctggt gctgctggtc aacctggtgc taaaggagaa    2220
agaggagcca aagggcctaa gggtgaaaac ggtgttgttg gtcccacagg ccccgttgga    2280
gctgctggcc cagctggtcc aaatggtccc cccggtcctg ctggaagtcg tggtgatgga    2340
ggcccccctg gtatgactgg tttccctggt gctgctggac ggaccggtcc cccaggaccc    2400
tctggtattt ctggccctcc tggtcccect ggtcctgctg ggaagaagg gcttcgtggt    2460 cctcgtggtg accaaggtcc agttggccga actggagaag taggtgcagt tggtcccect    2520 ggcttcgctg gtgagaaggg tccctctgga gaggctggta ctgctggacc tcctggcact    2580
ccaggtcctc agggtcttct tggtgctcct ggtattctgg gtctccctgg ctcgagaggt    2640
gaacgtggtc taccaggtgt tgctggtgct gtgggtgaac ctggtcctct tggcattgcc    2700
ggccctcctg gggcccgtgg tcctcctggt gctgtgggta gtcctggagt caacggtgct    2760
cctggtgaag ctggtcgtga tggcaaccct gggaacgatg gtccccagg tcgcgatggt    2820 caacccggac acaagggaga gcgcggttac cctggcaata ttggtcccgt tggtgctgca    2880
ggtgcacctg gtcctcatgg ccccgtgggt cctgctggca acatggaaa ccgtggtgaa    2940 actggtccct ctggtcctgt tggtcctgct ggtgctgttg gcccaagagg tcctagtggc    3000
ccacaaggca ttcgtggcga taagggagag cccggtgaaa aggggcccag aggtcttcct    3060
ggcttaaagg gacacaatgg attgcaaggt ctgctggta tcgctggtca ccatggtgat    3120
caaggtgctc ctggctccgt gggtcctgct ggtcctaggg gccctgctgg tccttctggc    3180
cctgctggaa aagatggtcg cactggacat cctggtacag ttggacctgc tggcattcga    3240
ggccctcagg gccaccaagg ccctgctggc cccctggtc ccctggccc tcctggacct    3300 ccaggtgtaa gcggtggtgg ttatgacttt ggttacgatg gagacttcta cagggctgac    3360
cagcctcgct cagcaccttc tctcagaccc aaggactatg aagttgatgc tactctgaag    3420
tctctcaaca accagattga gacccttctt actcctgaag gctctagaaa gaacccagct    3480
cgcacatgcc gtgacttgag actcagccac ccagagtgga gcagtggtta ctactggatt    3540
gaccctaacc aaggatgcac tatggatgct atcaaagtat actgtgattt ctctactggc    3600
gaaacctgta tccgggccca acctgaaaac atcccagcca gaactggta taggagctcc    3660 aaggacaaga aacacgtctg gctaggagaa actatcaatg ctggcagcca gtttgaatat    3720
aatgtagaag gagtgacttc caaggaaatg gctacccaac ttgccttcat gcgcctgctg    3780
gccaactatg cctctcagaa catcacctac cactgcaaga acagcattgc atacatggat    3840
gaggagactg gcaaccctga aaaggctgtc attctacagg gctctaatga tgttgaactt    3900
gttgctgagg gcaacagcag gttcacttac actgttcttg tagatggctg ctctaaaaag    3960
acaaatgaat ggggaaagac aatcattgaa tacaaaacaa ataagccatc acgcctgccc    4020
ttccttgata ttgcaccttt ggacatcggt ggtgctgacc aggaattctt tgtggacatt    4080
ggcccagtct gtttcaaata a                                             4101
```

<210> SEQ ID NO 5
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 5
gcggccgcca ccatgctcag ctttgtggat acgcgga            37

<210> SEQ ID NO 6
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 6
actagtttat ttgaaacaga ctgggccaat            30

<210> SEQ ID NO 7
<211> LENGTH: 4257
<212> TYPE: DNA
<213> ORGANISM: Homo sapiens

<400> SEQUENCE: 7
atgattcgcc tcggtgctcc ccagtcgctg gtgctgctga cgctgctcgt cgccgctgtc            60
cttcggtgtc agggccagga tgtccggcaa ccaggaccaa agggacagaa aggagaacct            120
ggagacatca aggatattgt aggacccaaa ggacctcctg gcctcagggg acctgcaggg            180
gaacaaggac ccagagggga tcgtggtgac aaaggtgaaa aaggtgcccc tggacctcgt            240
ggcagagatg gagaacctgg gaccctggga atcctggcc ccctggtcc tcccggcccc            300 cctggtcccc ctggtcttgg tggaaacttt gctgcccaga tggctggagg atttgatgaa            360
aaggctggtg gcgcccagtt gggagtaatg caaggaccaa tgggcccat gggacctcga            420 ggacctccag gccctgcagg tgctcctggg cctcaaggat tcaaggcaa tcctggtgaa            480 cctggtgaac ctggtgtctc tggtcccatg ggtccccgtg gtcctcctgg tccccctgga            540
aagcctggtg atgatggtga agctggaaaa cctggaaaag ctggtgaaag gggtccgcct            600
ggtcctcagg gtgctcgtgg tttcccagga accccaggcc ttcctggtgt caaaggtcac            660
agaggttatc caggcctgga cggtgctaag ggagaggcgg gtgctcctgg tgtgaagggt            720
gagagtggtt ccccgggtga aacggatct ccgggcccaa tgggtcctcg tggcctgcct            780
ggtgaaagag gacggactgg ccctgctggc gctgcgggtg cccgaggcaa cgatggtcag            840
ccaggccccg cagggcctcc gggtcctgtc ggtcctgctg gtggtcctgg cttccctggt            900
gctcctggag ccaagggtga agccggcccc actggtgccc gtggtcctga aggtgctcaa            960
ggtcctcgcg gtgaacctgg tactcctggg tccctgggc tgctggtgc ctccggtaac            1020 cctgaacag atgaattcc tggagccaaa ggatctgctg gtgctcctgg cattgctggt            1080
gctcctggct tccctgggcc acggggccct cctggccctc aaggtgcaac tggtcctctg            1140
ggcccgaaag gtcagacggg tgaacctggt attgctggct tcaaaggtga acaaggcccc            1200
aagggagaac ctggccctgc tggccccag ggagcccctg acccgctgg tgaagaaggc            1260 aagagaggtg cccgtggaga gcctggtggc gttgggccca tcggtccccc tggagaaaga            1320
ggtgctcccg gcaaccgcgg tttcccaggt caagatggtc tggcaggtcc caagggagcc            1380
cctggagagc gagggcccag tggtcttgct ggccccaagg gagccaacgg tgaccctggc            1440
cgtcctggag aacctggcct tcctggagcc cggggtctca ctggccgcc tggtgatgct            1500 ggtcctcaag gcaaagttgg cccttctgga gcccctggtg aagatggtcg tcctggacct            1560
ccaggtcctc aggggctcg tgggcagcct ggtgtcatgg gtttccctgg ccccaaaggt            1620
gccaacggtg agcctggcaa agctggtgag aagggactgc ctggtgctcc tggtctgagg            1680

```
ggtcttcctg gcaaagatgg tgagacaggt gctgcaggac cccctggccc tgctggacct    1740
gctggtgaac gaggcgagca gggtgctcct gggccatctg ggttccaggg acttcctggc    1800
cctcctggtc ccccaggtga aggtggaaaa ccaggtgacc agggtgttcc cggtgaagct    1860
ggagcccctg gcctcgtggg tcccagggg gaacgaggtt tcccaggtga acgtggctct    1920
cccggtgccc agggcctcca ggtccccgt ggcctcccccg gcactcctgg cactgatggt    1980
cccaaaggtg catctggccc agcaggcccc cctggggctc agggccctcc aggtcttcag    2040
ggaatgcctg gcgagagggg agcagctggt atcgctgggc caaaggtga cagggtgac    2100
gttggtgaga aaggccctga gggagcccct ggaaaggatg gtggacgagg cctgacaggt    2160
cccattggcc ccctggcc agctggtgct aacggcgaga agggagaagt tggacctcct    2220
ggtcctgcag gaagtgctgg tgctcgtggc gctccgggtg aacgtggaga gactgggccc    2280
cccggaccag cgggatttgc tgggcctcct ggtgctgatg ccagcctgg ggccaagggt    2340
gagcaaggag aggccggcca gaaaggcgat gctggtgccc ctggtcctca gggcccctct    2400
ggagcacctg ggcctcaggg tcctactgga gtgactggtc ctaaaggagc ccgaggtgcc    2460
caaggcccc cgggagccac tggattccct ggagctgctg ccgcgttgg acccccaggc    2520
tccaatggca ccctggacc ccctggtccc cctggtcctt ctggaaaaga tggtcccaaa    2580
ggtgctcgag gagacagcgg cccccctggc cgagctggtg aacccggcct ccaaggtcct    2640
gctgaccccc ctggcgagaa gggagagcct ggagatgacg tccctctgg tgccgaaggt    2700
ccaccaggtc cccagggtct ggctggtcag agaggcatcg tcggtctgcc tgggcaacgt    2760
ggtgagagag gattccctgg cttgcctggc ccgtcgggtg agcccggcaa gcagggtgct    2820
cctggagcat ctggagacag aggtcctcct ggccccgtgg gtcctcctgg cctgacgggt    2880
cctgcaggtg aacctggacg agagggaagc cccggtgctg atggccccccc tggcagagat    2940
ggcgctgctg gagtcaaggg tgatcgtggt gagactggtg ctgtgggagc tcctggagcc    3000
cctgggcccc ctggctcccc tggccccgct ggtccaactg gcaagcaagg agacagagga    3060
gaagctggtg cacaaggccc catgggaccc tcaggaccag ctggagcccg ggaatccag    3120
ggtcctcaag gccccagagg tgacaaagga gaggctggag agcctggcga gagaggcctg    3180
aagggacacc gtggcttcac tggtctgcag ggtctgcccg ccctcctgg tccttctgga    3240
gaccaaggtg cttctggtcc tgctggtcct ctggccccta gagtcctcc tggccccgtc    3300
ggtccctctg gcaaagatgg tgctaatgga atccctggcc ccattgggcc tcctggtccc    3360
cgtggacgat caggcgaaac cggccctgct ggtcctcctg gaaatcctgg accccctggt    3420
cctccaggtc ccccctggccc tggcatcgac atgtccgcct ttgctggctt aggcccgaga    3480
gagaagggcc ccgaccccct gcagtacatg cgggccgacc aggcagccgg tggcctgaga    3540
cagcatgacg ccgaggtgga tgccacactc aagtccctca caaccagat tgagagcatc    3600
cgcagcccccg agggctcccg caagaaccct gctcgcacct gcagagacct gaaactctgc    3660
caccctgagt ggaagagtgg agactactgg attgacccca accaaggctg caccttggac    3720
gccatgaagg ttttctgcaa catggagact ggcgagactt gcgtctaccc caatccagca    3780
aacgttccca gaagaactg gtggagcagc aagagcaagg agaagaaaca catctggttt    3840
ggagaaacca tcaatggtgg cttccatttc agctatggag atgacaatct ggctcccaac    3900
actgccaacg tccagatgac cttcctacgc ctgctgtcca cggaaggctc ccagaacatc    3960
acctaccact gcaagaacag cattgcctat ctggacgaag cagctggcaa cctcaagaag    4020
gccctgctca tccagggctc caatgacgtg agatccgggg cagagggcaa tagcaggttc    4080
```

```
acgtacactg ccctgaagga tggctgcacg aaacataccg gtaagtgggg caagactgtt    4140
atcgagtacc ggtcacagaa gacctcacgc ctccccatca ttgacattgc acccatggac    4200
ataggagggc ccgagcagga attcggtgtg gacatagggc cggtctgctt cttgtaa       4257

<210> SEQ ID NO 8
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 8
ggccccgcgg tgagccatga ttcgcctcg                                        29

<210> SEQ ID NO 9
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 9
tctagattac aagaagcaga ccggccctat                                       30

<210> SEQ ID NO 10
<211> LENGTH: 4401
<212> TYPE: DNA
<213> ORGANISM: Homo sapiens

<400> SEQUENCE: 10
atgatgagct ttgtgcaaaa ggggagctgg ctacttctcg ctctgcttca tcccactatt      60
attttggcac aacaggaagc tgttgaagga ggatgttccc atcttggtca gtcctatgcg     120
gatagagatg tctggaagcc agaaccatgc caaatatgtg tctgtgactc aggatccgtt     180
ctctgcgatg acataatatg tgacgatcaa gaattagact gccccaaccc agaaattcca     240
tttggagaat gttgtgcagt ttgcccacag cctccaactg ctcctactcg ccctcctaat     300
ggtcaaggac ctcaaggccc caagggagat ccaggccctc ctggtattcc tgggagaaat     360
ggtgaccctg gtattccagg acaaccaggg tcccctggtt ctcctggccc cctggaatc     420 tgtgaatcat gccctactgg tcctcagaac tattctcccc agtatgattc atatgatgtc     480
aagtctggag tagcagtagg aggactcgca ggctatcctg accagctggg cccccaggc     540 cctcccggtc cccctggtac atctggtcat cctggttccc ctggatctcc aggataccaa     600 ggacccccctg gtgaacctgg gcaagctggt ccttcaggcc ctccaggacc tcctggtgct     660
ataggtccat ctggtcctgc tggaaaagat ggagaatcag gtagaccggg acgacctgga     720
gagcgaggat tgcctggacc tccaggtatc aaaggtccag ctgggataccc tggattccct     780 ggtatgaaag acacagagg cttcgatgga cgaaatggaa aaagggtga acaggtgct      840 cctggattaa agggtgaaaa tggtcttcca ggcgaaaatg gagctcctgg acccatgggt     900
ccaagagggg ctcctggtga gcgaggacgg ccaggacttc tggggctgc aggtgctcgg    960 ggtaatgacg gtgctcgagg cagtgatggt caaccaggcc ctcctggtcc tcctggaact    1020
gccggattcc ctggatcccc tggtgccaag ggtgaagttg gacctcagg gtctcctggt    1080 tcaaatggtg cccctggaca agaggagaaa cctggacctc agggcacagc tggtgctcaa    1140
ggtcctcctg gccctcctgg gattaatggt agtcctggtg gtaaaggcga aatgggtccc    1200
```

```
gctggcattc ctggagctcc tggactgatg ggagcccggg gtcctccagg accagccggt    1260
gctaatggtg ctcctggact gcaggtggt gcaggtgagc ctggtaagaa tggtgccaaa    1320
ggagagcccg gaccacgtgg tgaacgcggt gaggctggca ttccaggtgt tccaggagct    1380
aaaggcgaag atggcaagga tggatcacct ggagaacctg gtgcaaatgg cttccagga    1440 gctgcaggag aaaggggtgc ccctgggttc cgaggacctg ctggaccaaa tggcatccca    1500
ggagaaaagg gtcctgctgg agagcgtggt gctccaggcc ctgcagggcc cagaggagct    1560
gctggagaac ctggcagaga tggcgtccct ggaggtccag gaatgagggg catgcccgga    1620
agtccaggag gaccaggaag tgatgggaaa ccagggcctc ccggaagtca aggagaaagt    1680
ggtcgaccag gtcctcctgg gccatctggt ccccgaggtc agcctggtgt catgggcttc    1740
cccggcccta aggaaatga tggtgctcct ggtaagaatg gagaacgagg tggccctgga    1800
ggacctggcc ctcagggtcc tcctggaaag aatggtgaaa ctggacctca gggaccccca    1860
gggcctactg ggcctggtgg tgacaaagga gacacaggac cccctggtcc acaaggatta    1920
caaggcttgc ctggtacagg tggtcctcca ggagaaaatg gaaaacctgg ggaaccaggt    1980
ccaaagggtg atgccggtgc acctggagct ccaggaggca aggtgatgc tggtgcccct    2040 ggtgaacgtg gacctcctgg attggcaggg gccccaggac ttagaggtgg agctggtccc    2100 cctggtccccg aaggaggaaa gggtgctgct ggtcctcctg gccacctgg tgctgctggt    2160 actcctggtc tgcaaggaat gcctggagaa agaggaggtc ttggaagtcc tggtccaaag    2220
ggtgacaagg gtgaaccagg cggtccaggt gctgatggtg tcccagggaa agacggccca    2280 aggggtcctga ctggtcctat tggtcctcct ggcccagctg gccagcctgg agataaggt    2340 gaaggtggtg ccccggact tccaggtata gctggacctc gtggtagccc tggtgagaga    2400
ggtgaaactg gccctccagg acctgctggt ttccctggtg ctcctggaca gaatggtgaa    2460
cctggtggta aggagaaag aggggctccg ggtgagaaag gtgaaggag ccctcctgga    2520 gttgcaggac cccctggagg ttctggacct gctggtcctc ctggtccccca aggtgtcaaa    2580 ggtgaacgtg gcagtcctgg tggacctggt gctgctggct ccctggtgc tcgtggtctt    2640 cctggtcctc ctggtagtaa tggtaaccca ggaccccag gtcccagcgg ttctccaggc    2700
aaggatgggc cccaggtcc tgcgggtaac actggtgctc ctggcagccc tggagtgtct    2760 ggaccaaaaag gtgatgctgg ccaaccagga gagaagggat cgcctggtgc ccagggccca    2820
ccaggagctc caggcccact tgggattgct gggatcactg gagcacgggg tcttgcagga    2880
ccaccaggca tgccaggtcc tagggggaagc cctggccccc aggtgtcaa gggtgaaagt    2940 gggaaaccag gagctaacgg tctcagtgga gaacgtggtc cccctggacc ccagggtctt    3000
cctggtctgg ctggtacagc tggtgaacct ggaagagatg gaaaccctgg atcagatggt    3060
cttccaggtc gagatggatc tcctggtggc aagggtgatc gtggtgaaaa tggctctcct    3120
ggtgcccctg gcgctcctgg tcatccgggc ccacctggtc ctgtcggtcc agctggaaag    3180
agtggtgaca gaggagaaag tggccctgct ggccctgctg tgctcccgg tcctgctggt    3240 tcccgaggtg ctcctggtcc tcaaggccca cgtggtgaca aggtgaaac aggtgaacgt    3300 ggagctgctg gcatcaaagg acatcgagga ttccctggta atccaggtgc cccaggttct    3360
ccaggccctg ctggtcagca gggtgcaatc ggcagtccag gacctgcagg ccccagagga    3420
cctgttggac ccagtggacc tcctggcaaa gatggaacca gtggacatcc aggtccatt    3480 ggaccaccag ggcctcgagg taacagaggt gaaagaggat ctgagggctc ccaggccac    3540 ccagggcaac caggccctcc tggacctcct ggtgcccctg gtccttgctg tggtggtgtt    3600
```

```
ggagccgctg ccattgctgg gattggaggt gaaaaagctg gcggttttgc cccgtattat      3660
ggagatgaac caatggattt caaaatcaac accgatgaga ttatgacttc actcaagtct      3720
gttaatggac aaatagaaag cctcattagt cctgatggtt ctcgtaaaaa ccccgctaga      3780
aactgcagag acctgaaatt ctgccatcct gaactcaaga gtggagaata ctgggttgac      3840
cctaaccaag gatgcaaatt ggatgctatc aaggtattct gtaatatgga aactggggaa      3900
acatgcataa gtgccaatcc tttgaatgtt ccacggaaac actggtggac agattctagt      3960
gctgagaaga aacacgtttg gtttggagag tccatggatg gtggttttca gtttagctac      4020
ggcaatcctg aacttcctga agatgtcctt gatgtgcagc tggcattcct tcgacttctc      4080
tccagccgag cttcccagaa catcacatat cactgcaaaa atagcattgc atacatggat      4140
caggccagtg gaaatgtaaa gaaggccctg aagctgatgg ggtcaaatga aggtgaattc      4200
aaggctgaag gaaatagcaa attcacctac acagttctgg aggatggttg cacgaaacac      4260
actggggaat ggagcaaaac agtctttgaa tatcgaacac gcaaggctgt gagactacct      4320
attgtagata ttgcacccta tgacattggt ggtcctgatc aagaatttgg tgtggacgtt      4380
ggccctgttt gcttttata a                                                4401

<210> SEQ ID NO 11
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 11
gcggccgcca ccatgatgag ctttgtgcaa aagggga                              37

<210> SEQ ID NO 12
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 12
tctagattat aaaaagcaaa cagggccaac                                      30
```

METHODS OF PRODUCING PROTEINS HAVING TRIPLE-HELIX STRUCTURE

CROSS REFERENCES

This application is a 371 National Phase of International Patent Application Serial No. PCT/JP2006/306941 filed Mar. 31, 2006 which claims priority to Japanese Patent Application Serial No. 2005-102999 filed Mar. 31, 2005, both of which are incorporated herein by reference in their entirety noting that the current application controls to the extent there is any contradiction with any earlier applications and to which applications we claim priority.

TECHNICAL FIELD

The present invention relates to methods of producing proteins having a triple-helix structure. More specifically, the present invention relates to methods of producing human collagen or partial peptides of human collagen. An objective of the present invention is to provide human collagen and partial peptides of human collagen that are safe for the living body and can be easily purified and obtained, and methods of producing them. More specifically, the present invention is to provide methods of producing human collagen and partial peptides thereof, by stably transducing Chinese hamster ovary (CHO) cells with a mammalian expression vector into which human collagen cDNA has been inserted.

BACKGROUND ART

Collagen is a protein that is distributed to almost all tissues of the body including the skin, bone and cartilage, and is well known to play important functions such as maintaining structures of tissues and organs by providing scaffolds for cells. Meanwhile, collagen is a bioabsorbable material that is decomposed by collagenases secreted from fibroblasts and collagenases present in phagocytes. Collagen is considered to be useful as a biomaterial because it is a biocompatible and bioabsorbable material as described above. Thus far, collagen has been used as a biomaterial for covering wounded skin and is reported to improve healing (Non-Patent Documents 1 and 2).

Forty percent of total collagen exists in the skin, and 70% or more of the dry weight of the skin and tendon is collagen; thus, collagen is important for developing artificial skin. It is applied as a useful material for cell and organ culture techniques, which gives great expectation in its applications in the booming field of regeneration medicine. It has been also pointed out that collagen (type II collagen) may be used to suppress articular rheumatism by oral intake (Non-Patent Documents 3 and 4). As a source material for such collagen, those derived from tissues of large non-human animals such as pigs and cows have been mainly used.

[Non-Patent Document 1] Surg. Forum, 10, 303 (1960)
[Non-Patent Document 2] J. Surg. Res., 10, 485-491 (1970)
[Non-Patent Document 3] Lancet, 342, 799 (1993)
[Non-Patent Document 4] Science, 261, 1727-1730 (1993)
[Patent Document 1] Japanese Patent Application Kokai Publication No. (JP-A) H10-179169 (unexamined, published Japanese patent application)

DISCLOSURE OF THE INVENTION

Problems to be Solved by the Invention

As described above, collagen is useful as a biomaterial or medicine for regeneration therapy and live organ transplantation, but the collagen used so far is derived from tissues of large non-human animals such as pigs and cows. Although collagen is a protein with low immunogenicity by nature, it is reported that when collagen from a xenogeneic animal is transplanted, implanted or administered as a biomaterial, immune reactions are induced at a low frequency (J. Immunol., 136, 877-882 (1986), Biomaterials, 11, 176-180 (1990)). In addition, the use of cow-derived collagen has become impossible due to the problem of prion contamination in cows. Furthermore, there is no guarantee that problems similar to prion contamination will not occur in animals such as pigs which are currently used for collagen extraction. From the above-mentioned aspects, it is preferable to use human-derived collagen as a biomaterial to be directly applied to the human body. However, extraction and purification of collagen from human tissues not only have ethical and technical problems, but is also qualitatively problematic in that the collagen obtained forms unspecific cross-linkages and is difficult to purify.

In order to obtain non-immunogenic collagen that is free from risk of pathogen contamination and easy to isolate and purify, collagen production using gene recombination techniques has been studied (Biochem. Soc., 28, 350-353 (2000)). However, it is very complicated to prepare an expression vector for introducing into host cells, a cDNA encoding a collagen molecule whose molecular weight is more than 100,000. In addition, conventional methods have low productivity and are far from practical application. Furthermore, it is known that collagen molecules have a triple-helix structure in which three peptides are associated. This structure is formed as a result of several modifications to primary translation products of the gene (N. Engl. J. Med., 311, 376-386 (1984)); however, only specific cells are thought to have such modification ability.

Attempts have been made to produce recombinant human collagen by using mouse fibroblasts, hamster lung cells and the like as a host (Proc. Natl. Acad. Sci. USA., 84, 764-768 (1987), J. Biol. Chem., 264, 20683-20687 (1989)). Although the collagen produced in these examples have a normal molecular structure, they are mixed collagen molecules of collagen gene products from both human and the host cell. In an example where human type II collagen was expressed (Biochem. J., 298, 31-37 (1994)), the amount produced was as small as 0.5 to 1 mg per liter of culture medium, and the type II collagen expressed by the introduced cDNA was found to be contaminated with a significant amount of host-derived type II collagen. Thus, it was necessary to separate endogenous type II collagen from type II collagen derived from the introduced gene.

In addition to the above-mentioned examples, there are examples of expressing human collagen using yeasts (Japanese Patent Kohyo Publication No. (JP-A) H7-501939 (unexamined, published Japanese national phase publication corresponding to a non-Japanese international publication)), insect cells (Japanese Patent Application Kokai Publication No. (JP-A) H8-23979 (unexamined, published Japanese patent application)), *Bacillus brevis* (JP-A H11-178574), and *Escherichia coli* (JP-A 2002-325584), but the post-expression modifications of collagen peptides may be different from those made in animal cells. As mentioned above, no method reported so far is satisfactory as a gene recombination method for producing human collagen in terms of quantity and quality. In addition, there has not been any investigation on methods for producing large quantities of proteins with a triple-helix structure such as collagen.

The present invention was achieved in view of the above circumstances. An objective of the present invention is to provide methods for producing proteins with a triple-helix structure. More specifically, the objective is to provide methods for producing human collagen molecules that are easy to isolate and purify, and have substantially the same structure as natural collagen molecules, by synthesizing large amounts of human collagen protein in host cells introduced with a collagen gene incorporated in a high expression vector, where the large amounts of human collagen protein are derived from the introduced gene.

Means for Solving the Problems

The present inventors performed various studies to solve the above-mentioned problems. As a result, the inventors discovered that large amounts of human collagen hardly contaminated with host cell-derived collagen can be produced, by selecting from various mammalian cells a host cell that has low collagen expression and introducing a collagen gene construct into a vector capable of high exogenous gene expression, and thereby completed the present invention. There has been no report of collagen production methods that preferentially produce human collagen in host cells by massively expressing an introduced collagen gene.

Specifically, the present inventors successfully developed methods for producing a large amount of human collagen that do not require a complex purification process, by inserting a human collagen gene into a vector capable of highly expressing a foreign gene and then introducing the resultant construct into a host mammalian cell with low expression of collagen (a triple-helix structural protein), and thereby completed the present invention.

Specifically, the present invention provides:

[1] a method of producing a protein having a triple-helix structure, wherein the method comprises:
(a) introducing DNA encoding a protein having a triple-helix structure into a vector;
(b) transforming a mammalian cell by transfer of the gene vector; and
(c) culturing or breeding the transformant, and collecting the protein having a triple helix structure from the cell or culture supernatant thereof;
[2] the method of [1], wherein the protein having a triple-helix structure is human collagen or a partial peptide thereof;
[3] the method of [2], wherein the human collagen consists of at least one or more types of α chains;
[4] the method of [2], wherein the human collagen is human type I collagen;
[5] the method of [4], wherein the human type I collagen is a complex of α1 and α2 chains;
[6] the method of [2], wherein the human collagen is human type II collagen;
[7] the method of [2], wherein the human collagen is human type III collagen;
[8] the method of [1], wherein the DNA encoding a protein having a triple helix structure is at least a DNA selected from:
(a) a DNA comprising any one of the nucleotide sequences of SEQ ID NOs:1, 4, 7, and 10; and
(b) a DNA hybridizing under stringent conditions with a DNA comprising any one of the nucleotide sequences of SEQ ID NOs:1, 4, 7, and 10;
[9] the method of any one of [1] to [8], wherein the mammalian cell is a Chinese hamster ovary (CHO) cell;
[10] the method of any one of [1] to [8], wherein the mammalian cell is a human embryonic kidney (HEK293) cell;
[11] the method of any one of [1] to [10], wherein the vector to be introduced with the DNA encoding a protein having a triple helix structure is pNOW/CMV-AA;
[12] a human collagen produced according to the method of any one of [1] to [11];
[13] a vector introduced with at least one DNA selected from:
(a) a DNA comprising any one of the nucleotide sequences of SEQ ID NOs:1, 4, 7, and 10; and
(b) a DNA hybridizing under stringent conditions with DNA comprising any one of the nucleotide sequences of SEQ ID NOs:1, 4, 7, and 10;
[14] a mammalian cell carrying the vector of [13]; and
[15] a kit for producing a protein having a triple helix structure, wherein the kit comprises the vector of [13] or the mammalian cell of [14].

Figure 1:
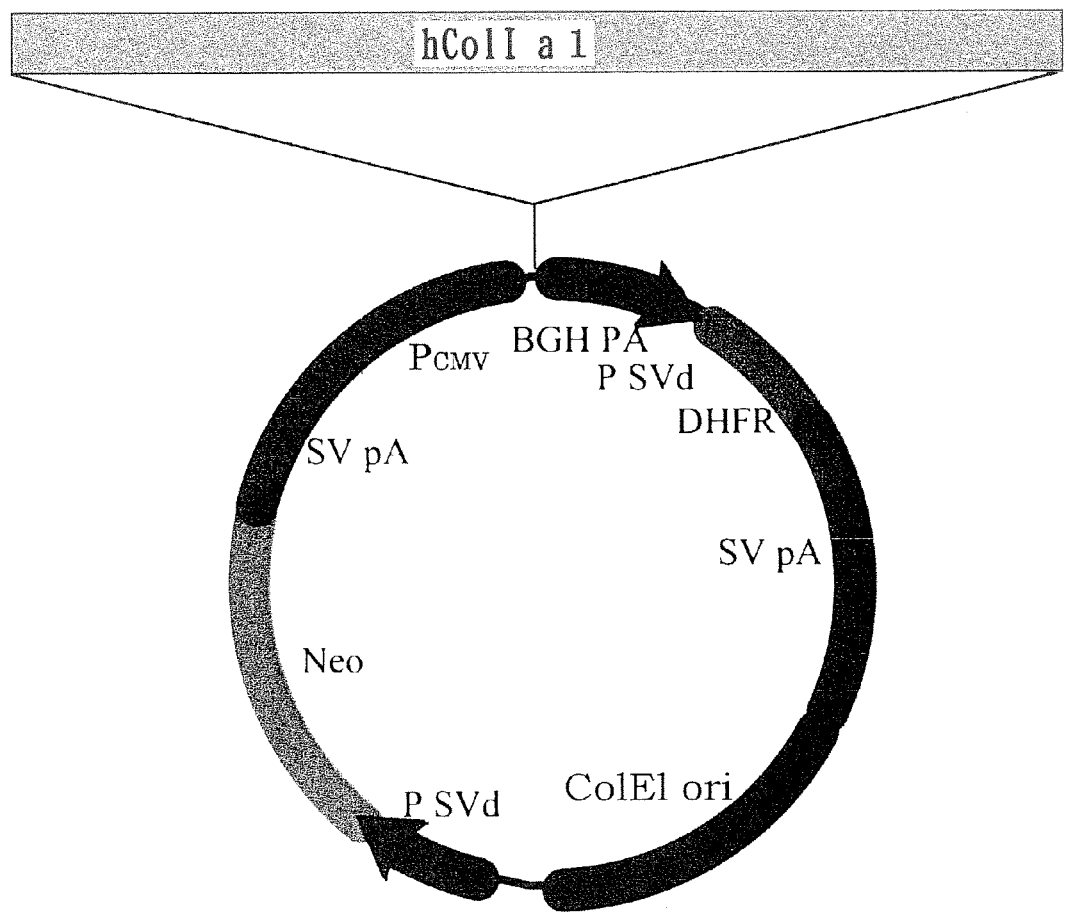
FIG. 1 shows an expression construct of an α1-chain of human type-I collagen. hColIa1: human type I collagen α1-chain cDNA, PCMV: cytomegalovirus promoter, BGHPA: poly (A) addition signal of bovine growth hormone gene, PSVd: simian virus 40 promoter devoid of enhancer, DHFR: mouse dihydrofolate reductase cDNA, SVpA: poly (A)-addition signal of simian virus 40, ColE1ori: replication origin of *Escherichia coli*, Neor: selection marker for mammalian cells (G418 resistance) and *Escherichia coli* (kanamycin resistance)

A. Detection by an antibody against the α1-chain of human type-I collagen, lane 1: human type I collagen (50 μg/mL), lane 2: recombinant type I collagen, lane 3: pepsin digested products of recombinant type I collagen.

B. Detection by an antibody against the α2-chain of human type-I collagen, lane 1: human type I collagen (10 μg/mL), lane 2: recombinant type I collagen, lane 3: pepsin-digested products of recombinant type I collagen.

Figure 8:
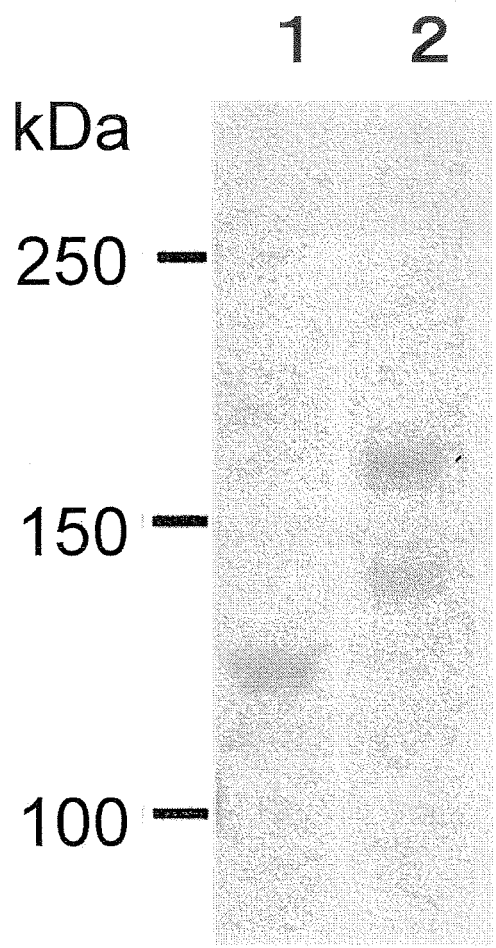

FIG. 8 is a photograph showing SDS-PAGE analysis of recombinant human type II collagen in culture supernatants. Lane 1: human type II collagen (100 μg/mL), lane 2: recombinant type II collagen.

Figure 9:
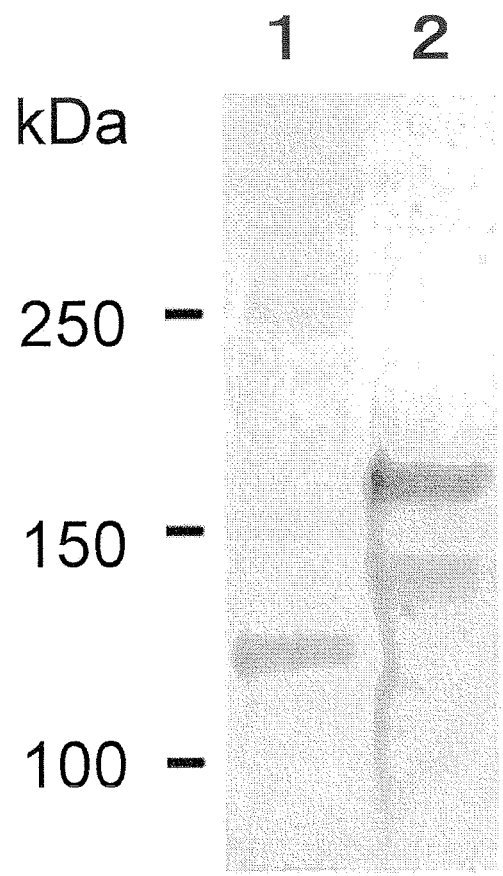

FIG. 9 is a photograph showing Western blot analysis of recombinant human type II collagen in culture supernatants. Lane 1: human type II collagen (10 μg/mL), lane 2: recombinant type II collagen (10 times diluted)

Figure 10:
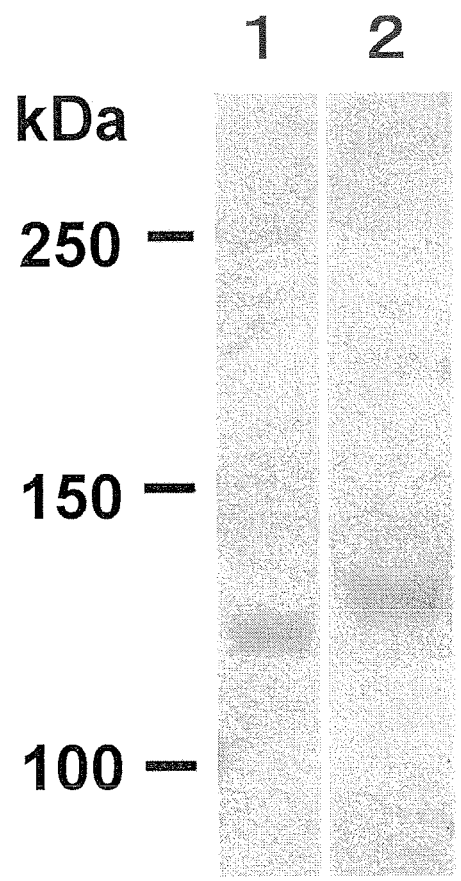

FIG. 10 is a photograph showing SDS-PAGE analysis of the pepsin-digested products of recombinant human type II collagen in culture supernatants. Lane 1: human type II collagen (100 μg/mL), lane 2: recombinant type II collagen (5 times concentrated).

Figure 11:
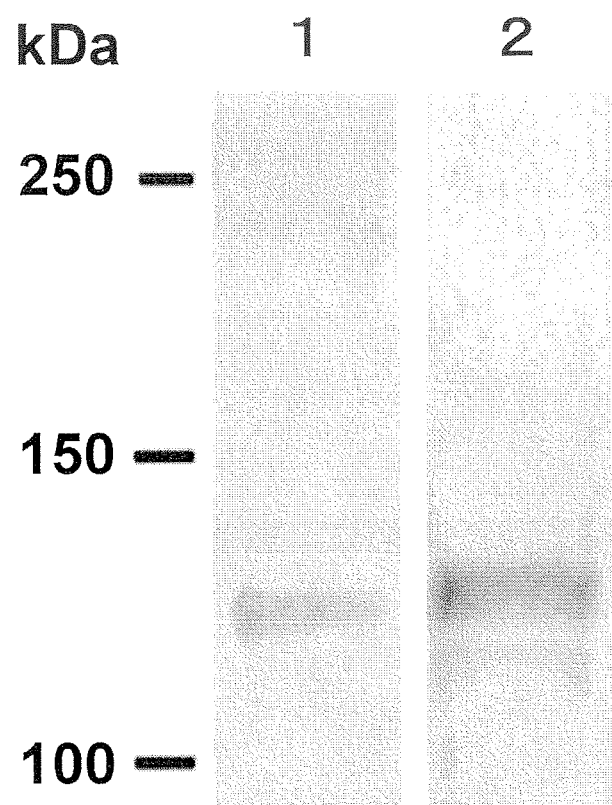

FIG. 11 is a photograph showing Western blot analysis of the pepsin-digested products of recombinant human type II collagen in culture supernatants. Lane 1: human type II collagen (10 μg/mL), lane 2: recombinant type II collagen.

Figure 12:
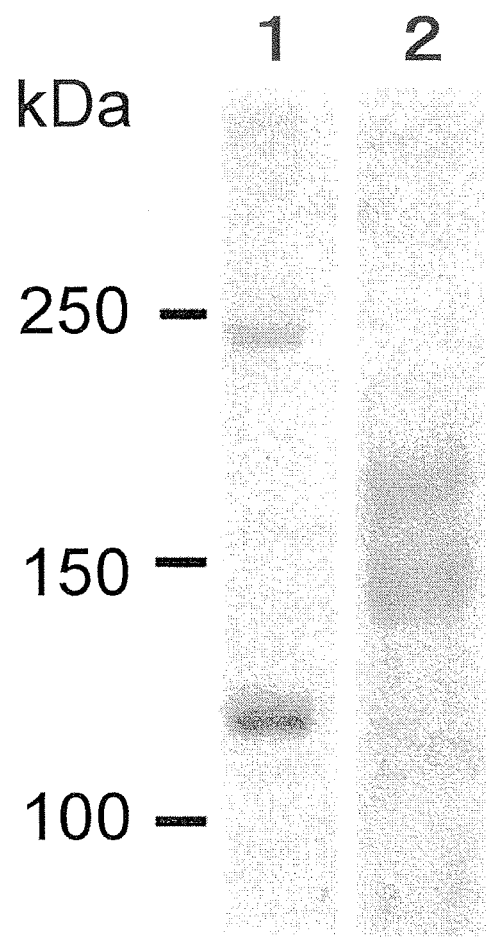

FIG. 12 is a photograph showing SDS-PAGE analysis of recombinant human type III collagen in culture supernatants. Lane 1: human type III collagen (100 μg/mL), lane 2: recombinant type III collagen.

Figure 13:
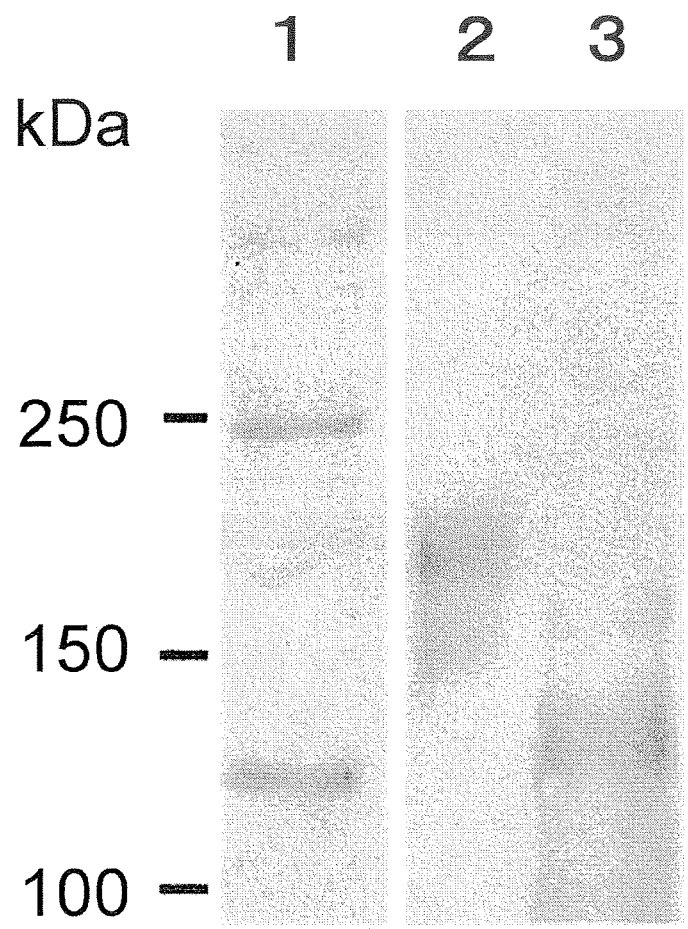

FIG. 13 is a photograph showing Western blot analysis of recombinant human type III collagen in culture supernatants and pepsin-digested products thereof. Lane 1: human type III collagen (10 μg/mL), lane 2: recombinant type III collagen (10 times diluted), lane 3: pepsin-digested products of recombinant type III collagen.

Figure 14:
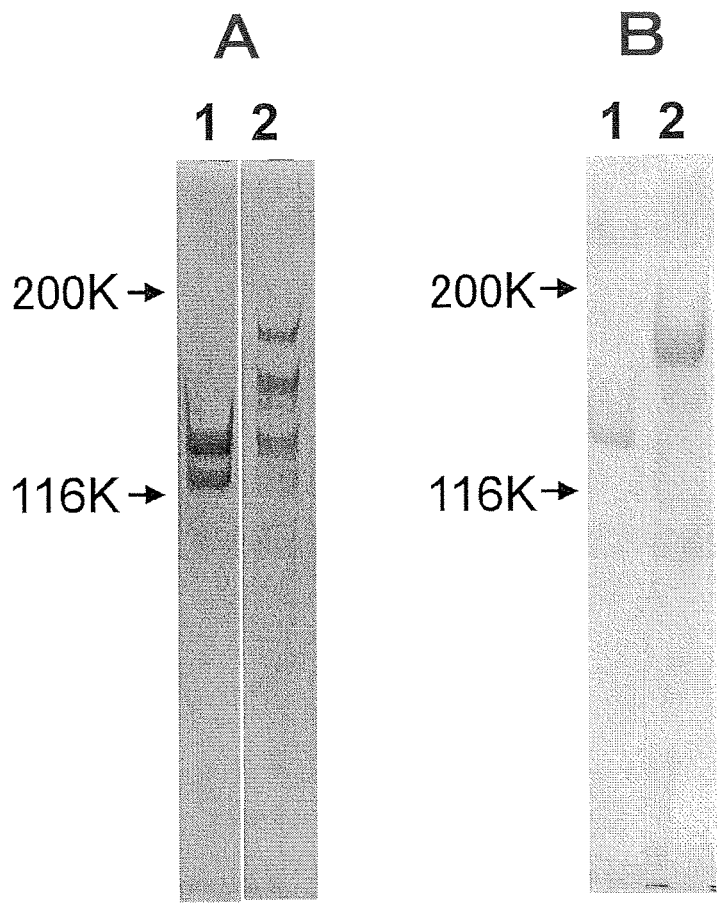

FIG. 14 is a photograph showing SDS-PAGE analysis of purified recombinant human type III collagen in culture supernatants.
A. Type I collagen, lane 1: human type I collagen, lane 2: recombinant type I collagen.
B. Type III collagen, lane 1: human type III collagen, lane 2: recombinant type III collagen.

BEST MODE FOR CARRYING OUT THE INVENTION

Herein below, the best mode to conduct the present invention is shown and the present invention is explained in more detail.

The present invention relates to methods of producing proteins having a triple-helix structure, comprises the steps of:
(a) introducing into a vector a DNA encoding a protein having a triple-helix structure;
(b) transforming a mammalian cell by transfer of the gene vector;
(c) culturing or breeding the transformant, and collecting proteins with a triple-helix structure from the cells or culture supernatants thereof.

"Proteins having a triple-helix structure" in the present invention are not specifically limited as long as they has a triple-helix structure, but are preferably collagen or collectin, and more preferably collagen. Proteins having a triple-helix structure may be proteins whose triple-helix structure is constructed during the steps of culture and production, or after the steps of culture and production by manipulations such as purification. It is also possible to produce large quantities of proteins that can form a triple-helix structure in a single-chain structural state.

More than 20 different types of collagen and about 25 types of constituting α chains are known. Genes encoding them have been cloned and nucleotide sequences thereof have been elucidated ("Connective Tissue and Its Heritable Disorders", pp 145-165, published by Weily-Liss Inc. (1992)). These genes can be introduced into a vector used in the present invention that can highly express foreign genes by gene recombination techniques known to those skilled in the art (for example, "Molecular Cloning" second edition, published by Cold Spring Harbor Laboratory Press (1989)). The human collagen cDNA used in the present invention may be any one of these cloned cDNAs of collagen, and includes cDNAs of partial collagen peptides.

The collagen of the present invention does not have a specifically limited origin, but mammal-derived collagen is preferable, and human-derived collagen is more preferable.

Furthermore, the collagen of the present invention also includes collagen whose amino acid sequence is partially modified by substitution, deletion, or such, or has an addition of a non-collagen-derived amino acid sequence. In addition, there are known methods for obtaining transduced cells expressing protein molecules by introducing a vector into host mammalian cells. Similar methods can be applied to the present invention.

The following method can be used to examine whether collagen is synthesized as a recombinant protein by cells introduced with the above-mentioned high exogenous gene expression vector. Specifically, collagen peptides can be identified by immunochemical methods such as Western blotting by using commercially available antibodies that specifically bind to human collagen. Collagen usually does not migrate according to molecular weight in SDS-polyacrylamide gel electrophoresis (Nature, 227, 680-685 (1970)). Thus, the reactivity of a sample with an anti-collagen antibody can be examined after the sample is electrophoresed simultaneously with collagen as a marker and transferred to a nylon membrane or a nitrocellulose membrane according to the method by Matsudaira et al. (J. Biol. Chem., 261, 10035-10038 (1987)). Further, whether a molecule having a triple-helix structure is present in the recombinant collagen products generated by the expression vector can be examined as follows.

Typical fibrous collagen is a three-chain molecule formed from three subunits (α chains), and has an intramolecular triple-helix structure. Further, collagen having a triple-helix structure is known to be resistant to pepsin digestion. Thus, the presence of three-chain molecules in a protein sample can be confirmed by digesting culture supernatants of cells introduced with the above-mentioned high exogenous gene expression vector with pepsin in an acidic condition, and examining whether the sample has a pepsin-resistant structure.

Specifically, in the present invention, pepsin-treated protein samples were subjected to SDS-polyacrylamide gel electrophoresis under reducing conditions. As a result, the obtained recombinant collagen was shown to have pepsin resistance similar to that of natural collagen, and thus collagen peptides having a pepsin-resistant property were expected to be contained in culture supernatants of cells introduced with a high exogenous gene expression vector. The above-mentioned results show that the expression vector of the present invention has ability to synthesize in host cells, collagen that has resistance to pepsin, which is a characteristic equivalent to collagen found in the living body.

Methods of producing and purifying the triple-helix structural proteins of the present invention are shown below, without being limited thereto.

Mammalian cells used as a host cell in the present invention are not particularly limited, but are preferably CHO cells or HEK293 cells.

Large-scale culture of CHO cells or HEK293 cells used in the present invention can be done by suspension culture. For example, $1\times10^8$ to $1\times10^9$ recombinant CHO cells introduced with a human collagen-expression vector containing a weakened neomycin phosphotransferase gene, mouse dihydrofolate reductase gene, and cDNA encoding human collagen or a partial peptide thereof can be cultured in a shaker flask or a spinner flask using 100 ml to 1 L of culture medium. After culturing these cells for an appropriate period of time, proteins can be extracted from the collected culture supernatants in large quantities.

In the culture supernatants of recombinant CHO cells introduced with the human collagen-expression vector containing a weakened neomycin phosphotransferase gene, mouse dihydrofolate reductase gene, and cDNA encoding human collagen or a partial peptide thereof, there exist not only three-chain collagen molecules with a triple-helix structure, but also collagen that has not formed into normal three-chain molecules. As mentioned above, collagen molecules that do not have a triple-helix structure are digested by pepsin. Thus, collagen molecules lacking a triple-helix structure can be removed by pepsin digestion. This treatment can also at the same time degrade and remove the non-collagen proteins in culture supernatants. By using the above-mentioned characteristics, non-collagen proteins as well as collagen lacking a triple-helix structure can be digested and removed by direct pepsin treatment of total proteins present in the culture supernatants of recombinant CHO cells introduced with a human collagen expression vector containing a weakened neomycin phosphotransferase gene, mouse dihydrofolate reductase gene, and cDNA encoding human collagen or a partial peptide thereof.

In the present invention, the human collagen of interest is all human collagens that are currently known, including type I to XXI collagens, and also includes partial peptides thereof. The type of collagen of the present invention is not particularly limited but includes, as representative examples, type I, type II, type III, type IV, type V, type VII, type IX, type XI, type XII, type XVII, and type XVIII, and preferably type I, type II, type III. Types I, IV, V, IX, and XI consist of two or three types of α chains, and types II, III, VII, XII, XVII, and XVIII consist of one type of a chain. They each have the following molecular composition: type I: $[\alpha1(I)]_2\alpha2(I)$, type II: $[\alpha1(II)]_3$, type III: $[\alpha1(III)]_3$, type IV: $[\alpha1(IV)]_2\alpha2(IV)$, type V: $[\alpha1(V)]_2\alpha2(V)$ and $\alpha1(V)\alpha2(V)\alpha3(V)$, type VII: $[\alpha1(VII)]_3$, type IX: a $1(IX)\alpha2(IX)\alpha3(IX)$, type XI: $\alpha1(XI)\alpha2(XI)\alpha3(XI)$, type XII: $[\alpha1(XII)]_3$, type XVII: $[\alpha1(XVII)]_3$, or type XVIII: $[\alpha1(XVIII)]_3$; however, the molecular composition of the collagen of the present invention is not particularly limited. Further, the molecular composition of collagen of the present invention is not restricted to that of natural collagen, and may be artificially composed of three different types of α chains.

The nucleotide sequence of a DNA encoding the α1 chain of type I collagen of the present invention is indicated in SEQ ID NO: 1, the nucleotide sequence of a DNA encoding the α2 chain of type I collagen is indicated in SEQ ID NO: 4, the nucleotide sequence of a DNA encoding the α1 chain of type II collagen is indicated in SEQ ID NO: 7, and the nucleotide sequence of a DNA encoding the α1 chain of type III collagen is indicated in SEQ ID NO: 10.

DNAs encoding the collagen of the present invention include oligonucleotides that have any one of the nucleotide sequences of SEQ ID NOs: 1, 4, 7, and 10, and preferably include oligonucleotides that selectively hybridize to oligonucleotides having any one of the nucleotide sequences of SEQ ID NOs: 1, 4, 7, and 10. "Selectively hybridizing" refers to nucleic acid molecules that hybridize with, form double strands with, or bind substantially to a molecule having a predetermined sequence (i.e. a second oligonucleotide) present in a DNA or RNA sample under hybridization conditions of appropriate stringency. The stringent conditions are, for example, usually conditions of 42° C., 2×SSC, and 0.1% SDS, preferably conditions of 50° C., 2×SSC, and 0.1% SDS, and more preferably conditions of 65° C., 0.1×SSC, and 0.1% SDS, but are not particularly limited to these conditions. Conditions affecting hybridization stringency may include plural factors such as temperature and salt concentration, and those skilled in the art can appropriately select these factors to achieve the most appropriate stringency.

Collagen produced by the present invention may be procollagen molecules in which a propeptide links to the N- and C-termini, or may be in a form in which the propeptide is removed.

In the present invention, "partial peptides of collagen" refers to polypeptides that are encoded by 20% or more (for example, 20, 30, 40, 50, 60, 70, 80, or 90%) of the polynucleotides of a collagen-encoding cDNA. The peptides also include those in which the collagen amino acid sequences are partially modified or those that have an added non-collagen amino acid sequence.

In the present invention, "mammalian cells with low collagen expression" refers to cells producing 50 ng/mL of collagen or less when cultured at a density of $1\times10^6$ cells/mL; and preferred examples are CHO cells and HEK293 cells. In the present invention, "high expression" refers to expression of 10 μg/mL of collagen or more, preferably expression of 50 μg/mL or more of collagen.

In the present invention, "high exogenous gene expression vector" refers to, for example, vectors comprising a weak drug-selectable marker gene in mammalian cells, such that the exogenous gene carried by the vector is selectively inserted into an actively transcribed region of chromosome in mammalian cells. Such vectors preferably include the pNOW/CMV-AA vector. The pNOW/CMV-AA vector is known in JP-A H10-179169. In the present invention, the culture method may be either suspension or adhesion culture.

All prior art literatures cited in the present specification are incorporated herein by reference.

Hereinbelow, the present invention will be described more specifically using Examples; however, it is not to be construed as being limited thereto.

Example 1

Preparation of the pNOW/CMV-AA Vector

The pNOW/CMV-AA vector used was prepared by a known method (JP-A H10-179169).

Example 2

Preparation of Collagen Expression Vectors (1):
Isolation of Human Type-I α1-Chain cDNA The human type-I α1-chain collagen gene has already been cloned, and the nucleotide sequence thereof has been reported (EMBL Gene Database Accession No: NM 000088). The sequence is shown in SEQ ID NO: 1. Human type-I α1 cDNA was amplified from human testis-derived cDNA by the polymerase chain reaction (PCR) method ("PCR Technology", published by Stockton Press (1989)). Specifically, the full-length sequence of SEQ ID NO: 1 was amplified by PCR using human testis-derived cDNA (Becton, Dickinson and Company) as a template and the oligonucleotides of SEQ ID NO: 2 (GCGGCCGCCACCATGTTCAGCTTTGTG-GACCTCCG) and SEQ ID NO: 3 (TTCTAGATTACAG-GAAGCAGACAGGGCCAA) as primers. More specifically, the reaction was carried out using a commercially available PCR amplification kit (TaKaRa LA Taq with GC Buffer: Takara Bio Inc.). The reaction mixture was heated at 94° C. for 5 minutes, and then subjected to 35 cycles of the following three steps: denaturation (94° C., 20 seconds), annealing of primers (60° C., 30 seconds), and amplification (72° C., 3 minutes 30 seconds), followed by an additional treatment at 72° C. for 7 minutes to end the reaction. Hereinafter, all the PCR reactions in the Examples were carried out in the same reaction cycle. The PCR product obtained was separated by agarose gel electrophoresis, and ligated into a cloning vector for PCR products (pT7Blue kits: Novagen Inc.) using a ligation kit (DNA ligation kit ver.2: Takara Bio Inc.). After the ligated DNA was introduced into *Escherichia coli* strain XL-I Blue, plasmid DNA was obtained by culturing ampicillin-resistant colonies appeared on LB agar medium (Difco Inc.). A DNA fragment encoding human type I α1-chain collagen was excised from the plasmid DNA, and ligated with a Not I and Xba I-digested product of the pNOW/CMV-AA vector prepared in Example 1, using DNA Ligation Kit ver.2. After the ligated DNA was introduced into *Escherichia coli* strain XL-I Blue, plasmid DNA (pNOW-hColIa1, FIG. 1) was obtained by culturing one ampicillin-resistant colony that appeared on LB agar medium.

Example 3

Figure 2:
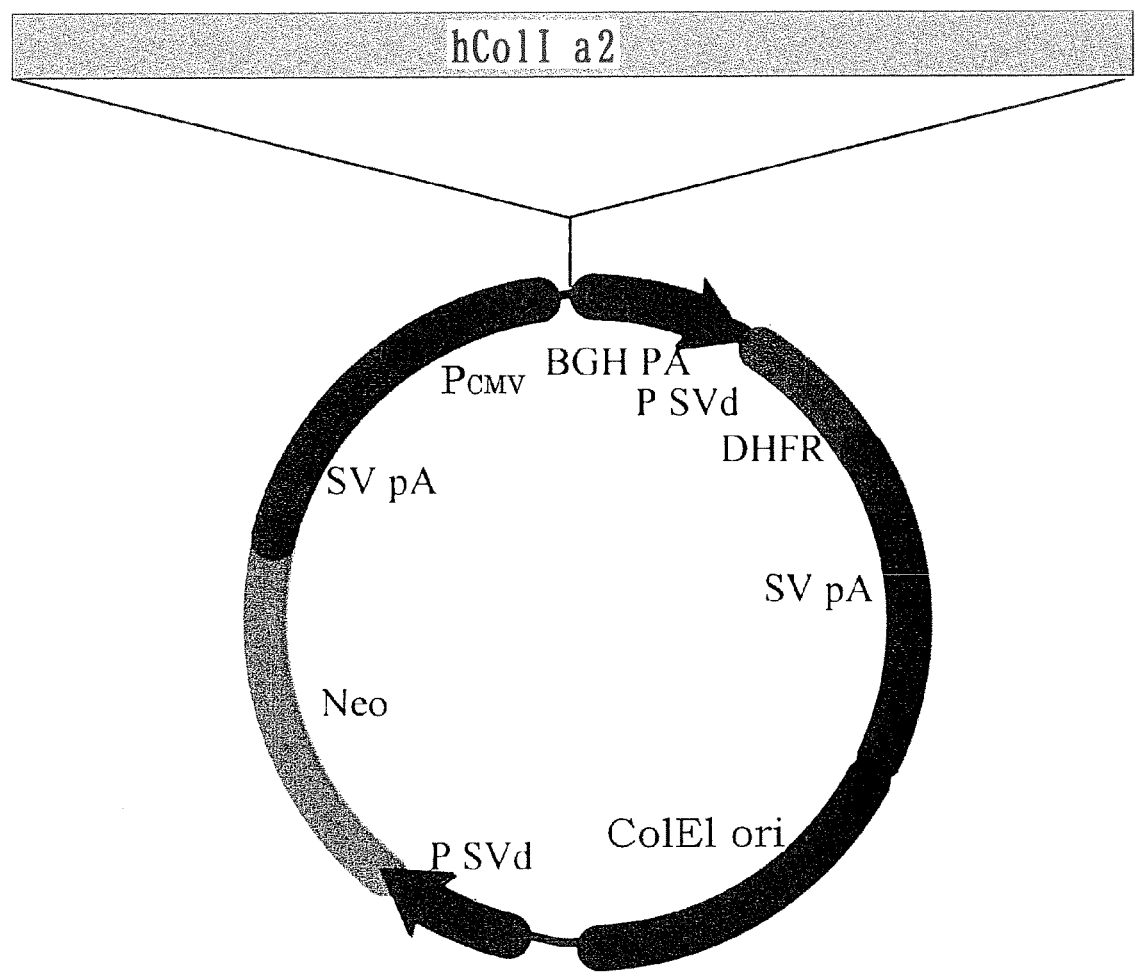
FIG. 2 shows an expression construct of an α2-chain of human type-I collagen. hColIa2: human type-I collagen α2-chain gene cDNA, PCMV: cytomegalovirus promoter, BGHPA: poly (A) addition signal of bovine growth hormone gene, PSVd: simian virus 40 promoter devoid of enhancer, DHFR: mouse dihydrofolate reductase cDNA, SVpA: poly (A) addition signal of simian virus 40, ColE1ori: replication origin of *Escherichia coli*, Neor: selection marker for mammalian cells (G418 resistance) and *Escherichia coli* (kanamycin resistance)

Preparation of Collagen Expression Vectors (2): Isolation of Human Type-I α2-Chain cDNA The human type-I α2-chain collagen gene has already been cloned, and its nucleotide sequence has been reported (EMBL Gene Database Accession No: NM 000089). The sequence is shown in SEQ ID NO: 4. The human type-I α2 cDNA was amplified from human liver-derived cDNA by PCR. Specifically, the full-length sequence of SEQ ID NO: 4 was amplified by PCR using human liver-derived cDNA (Wako Pure Chemical Industries, Ltd) as a template and the oligonucleotides of SEQ ID NO: 5 (GCGGCCGCCACCATGCT-CAGCTTTGTGGATACGCGGA) and SEQ ID NO: 6 (ACT-AGTTTATTTGAAACAGACTGGGCCAAT) as primers. The resultant PCR product was separated by agarose gel electrophoresis, and was ligated into a cloning vector for PCR products (pT7Blue kits: Novagen Inc.) by using a ligation kit (DNA ligation kit ver.2: Takara Bio Inc.). After the ligated DNA was introduced into the *Escherichia coli* strain XL-I Blue, plasmid DNA was obtained by culturing four ampicillin-resistant colonies that appeared on LB agar medium (Difco Inc.). A DNA fragment encoding human type-I α2-chain collagen was excised from the plasmid DNA, and ligated into pNOW/CMV-AA vector cleaved with Not I and Xba I using DNA Ligation Kit ver.2. After the ligated DNA was introduced into *Escherichia coli* strain XL-I Blue, plasmid DNA (pNOW-hColIa2, FIG. 2) was obtained by culturing one ampicillin-resistant colony that appeared on LB agar medium.

Example 4

Figure 3:
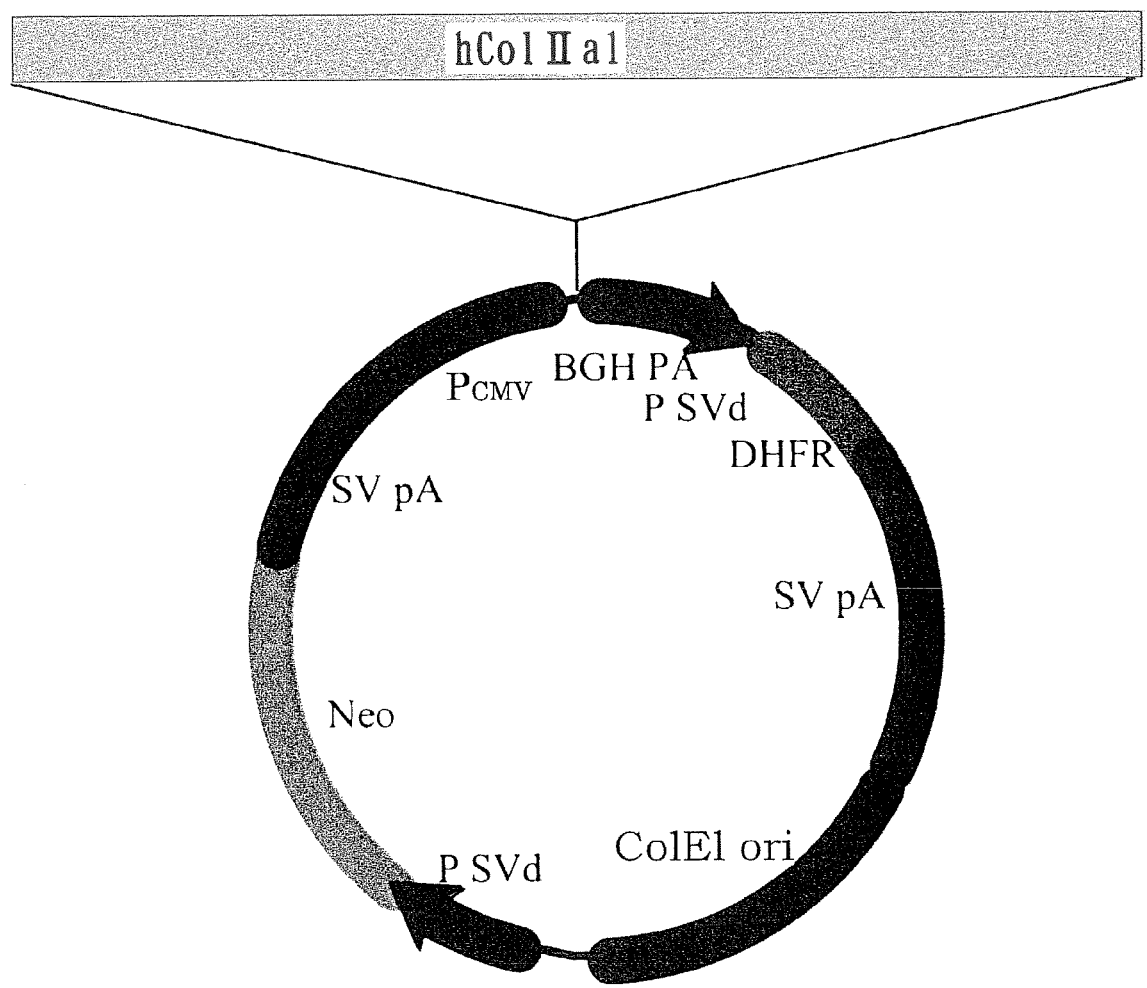
FIG. 3 shows an expression construct of an α1-chain of human type-II collagen. hColIIa1: human type-II collagen α1-chain cDNA, PCMV: cytomegalovirus promoter, BGHPA: poly(A) addition signal of bovine growth hormone gene, PSVd: simian virus 40 promoter devoid of enhancer, DHFR: mouse dihydrofolate reductase cDNA, SVpA: poly (A)-addition signal of simian virus 40, ColE1ori: replication origin of *Escherichia coli*, Neor: selection marker for mammalian cells (G418 resistance) and *Escherichia coli* (kanamycin resistance)

Preparation of Collagen-Expression Vector (3): Isolation of Human Type-II α1-Chain cDNA The human type-II α1-chain collagen gene has already been cloned, and its nucleotide sequence has been reported (EMBL Gene Database Accession No: NM 001844.1). The sequence is shown in SEQ ID NO: 7. Human type-II a1 cDNA was amplified from human testis-derived cDNA by PCR. Specifically, the full-length sequence of SEQ ID NO: 7 was amplified by PCR using human testis-derived cDNA (Becton, Dickinson and Company) as a template and the oligonucleotides of SEQ ID NO: 8 (GGCCCCGCGGTGAGCCAT-GATTCGCCTCG) and SEQ ID NO: 9 (TCTAGATTACAA-GAAGCAGACCGGCCCTAT) as primers. The PCR product obtained was separated by agarose gel electrophoresis, and ligated to a cloning vector for PCR products (pT7Blue kits: Novagen Inc.) using a ligation kit (DNA ligation kit ver.2: Takara Bio Inc.). After the ligated DNA was introduced into *Escherichia coli* strain XL-I Blue, plasmid DNA was obtained by culturing four ampicillin-resistant colonies that appeared on LB agar medium (Difco Inc.). A DNA fragment encoding human type-II α1-chain collagen was excised from the plasmid DNA, and ligated with pNOW/CMV-AA vector cleaved with Not I and Xba I using DNA Ligation Kit ver.2. After the ligated DNA was introduced into *Escherichia coli* strain XL-I Blue, plasmid DNA (pNOW-hColIIa1, FIG. 3) was obtained by culturing one ampicillin-resistant colony that appeared on LB agar medium.

Example 5

Figure 4:
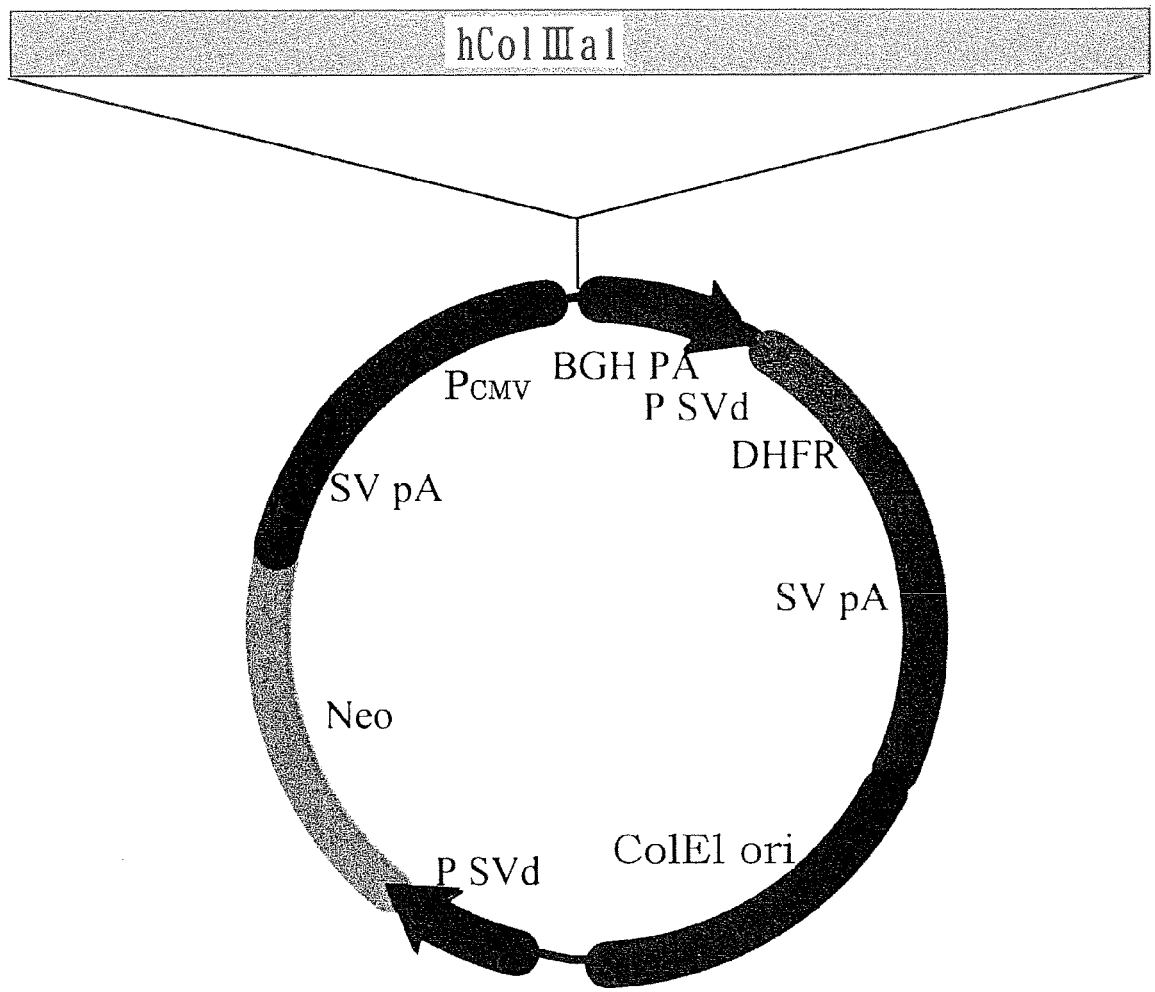
FIG. 4 shows an expression construct of an α1-chain of human type-III collagen. hColIIIa1: human type-III collagen α1-chain cDNA, PCMV: cytomegalovirus promoter, BGHPA: poly(A) addition signal of bovine growth hormone gene, PSVd: simian virus 40 promoter devoid of enhancer, DHFR: mouse dihydrofolate reductase cDNA, SVpA: poly (A) addition signal of simian virus 40, ColE1ori: replication origin of *Escherichia coli*, Neor: selection marker for mammalian cells (G418 resistance) and *Escherichia coli* (kanamycin resistance)

Preparation of Collagen Expression Vectors (4): Isolation of Human Type-III α1-Chain cDNA The human type-III α1-chain collagen gene has already been cloned, and its nucleotide sequence has been reported (EMBL Gene Database Accession No: X14420). The sequence is shown in SEQ ID NO: 10. Human type-III α1 cDNA was amplified from human liver-derived cDNA by PCR. Specifically, the full-length sequence of SEQ ID NO: 10 was amplified by PCR using human liver-derived cDNA (Wako Pure Chemical Industries, Ltd) as a template and the oligonucleotides of SEQ ID NO: 11 (GCGGCCGCCAC-CATGATGAGCTTTGTGCAAAAGGGGA) and SEQ ID NO: 12 (TCTAGATTATAAAAAGCAAACAGGGCCAAC) as primers. The PCR product obtained was separated by agarose gel electrophoresis, and ligated into a cloning vector for PCR products (pT7Blue kits III Novagen Inc.) using a ligation kit (DNA ligation kit ver.2: Takara Bio Inc.). After the ligated DNA was introduced into *Escherichia coli* strain XL-I Blue, plasmid DNA was obtained by culturing four ampicillin-resistant colonies that appeared on LB agar medium. A DNA fragment encoding human type-III α1-chain collagen was excised from the plasmid DNA, and ligated into pNOW/CMV-AA vector cleaved with Not I and Xba I using DNA Ligation Kit ver.2. After the ligated DNA was introduced into *Escherichia coli* strain XL-I Blue, plasmid DNA (pNOW-hColIIIa1, FIG. 4) was obtained by culturing one ampicillin-resistant colony that appeared on LB agar medium.

Example 6

Production of Human Type I Collagen: Transfer of the Human Type-I Collagen Gene Using Expression Vectors pNOW-hColIa1 and pNOW-hColIa2, and Establishment of Primary G418-Resistant Clones One microgram each of pNOW-hColIa1 and pNOW-hColIa2 obtained in Examples 2 and 3 was transferred into 1.5 million DHFR-deficient CHO cells (CHO DG44 cells; provided by Dr. Gail Urlaub) in a 25 cm² culture flask by the lipofectin method (Effectene Transfection Reagent, QIAGEN Inc.). The transfer method was carried out according to the manufacturer's instructions. After 48 hours, the cells were removed by trypsin treatment and the number of cells was counted. Then, $5 \times 10^5$ cells were diluted with 100 mL of Iscove's Modified Dulbecco's Medium containing 0.8 mg/mL G418 and 10% dialyzed fetal bovine serum, and then were seeded into ten 96-well microtiter plates (960 wells), followed by culturing at 37° C. for three weeks under the presence of 5% carbon dioxide gas. Live cells in 197 wells were transferred to 24-well plates with 1 mL of Iscove's Modified Dulbecco's Medium containing 0.8 mg/mL G418 and 10% dialyzed fetal bovine serum, and were cultured until confluent. After discarding culture supernatants, 1 mL of PBS (Invitrogen Inc.) was added to each well, and culture supernatants were discarded again. 0.5 mL of ProCHO4 (Takara Bio Inc.), a CD medium for CHO cells, was added to each well and cultured at 37° C. for 96 hours under the presence of 5% carbon dioxide gas. Subsequently, the amount of human type I collagen produced in the culture supernatants was examined.

Example 7

Quantitative Assay of the Human Type I Collagen Produced in pNOW-hColIa1- and pNOW-hColIa2-Transduced Cell Clones The amount produced was assayed by SDS-polyacrylamide gel electrophoresis. 12.5 µL of the culture supernatant was mixed with an equal volume of Tris-SDSβ-ME sample treatment solution (Daiichi Pure Chemicals Co., Ltd.), and heat-treated at 95° C. for 5 minutes. This mixture was loaded onto an SDS-polyacrylamide gel (PAGEL, ATTO Inc.) and fractionated by electrophoresis. After the electrophoresis, human type I collagen in the polyacrylamide gel was detected and quantified by treating the gel with Coomassie Brilliant Blue Staining Solution (Amersham Biosciences). As a comparative control, 12.5 µg/mL to 100 µg/mL of human type I collagen (Cosmo Bio Co., Ltd.) treated in the same way was used.

Example 8

Production of Human Type I Collagen

Among the G418-resistant cell lines, a cell clone that produced the largest amount of human type I collagen was stabilized by passaging and culturing. The level of human type I collagen produced was 85 µg/mL culture medium (four days).

Example 9

SDS-PAGE Analysis of Recombinant Human Type I Collagen in Culture Supernatants

Figure 5:
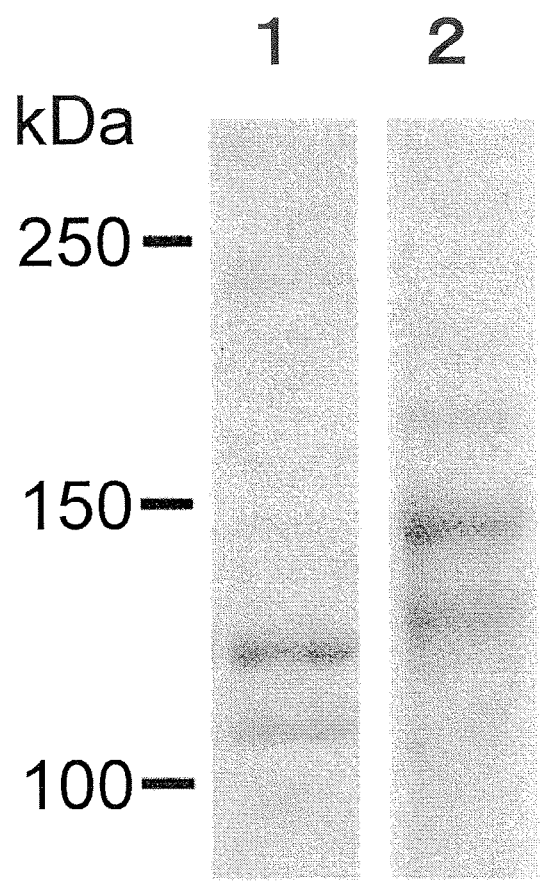
FIG. 5 is a photograph showing SDS-PAGE analysis of recombinant human type I collagen in culture supernatants. Lane 1: human type I collagen (100 μg/mL), lane 2: recombinant type I collagen.

The cell clone massively producing human type I collagen obtained by gene amplification was adjusted to $1 \times 10^6$ cells/mL in a 25 cm² culture flask using the cell culture solution IS CHO-CD (IS Japan Co., Ltd.). After culturing at 37° C. for 96 hours under the presence of 5% carbon dioxide gas, the culture fluid was collected. The cells were removed by centrifugation to obtain a culture supernatant. 12.5 µL of the culture supernatant was mixed with an equal volume of Tris-SDSβ-ME sample treatment solution (Daiichi Pure Chemicals Co., Ltd.), and heat-treated at 95° C. for 5 minutes. This mixture was loaded onto an SDS-polyacrylamide gel (PAGEL, ATTO Inc.) and fractionated by electrophoresis. The SDS-polyacrylamide gel electrophoresis described below was carried out in the same way. After the electrophoresis was finished, human type I collagen in the polyacrylamide gel was detected by treating the gel with Coomassie Brilliant Blue Staining Solution (Amersham Biosciences). 100 µg/mL of human type I collagen treated in the same way was used as a comparative control. FIG. 5 shows the result of SDS-PAGE analysis of the culture supernatant obtained from the human type I collagen-producing cell clone. 150- and 170-kDa polypeptides which may be recombinant human type I collagen α1 chains, and 130- and 150-kDa polypeptides which may be recombinant human type I collagen α2 chains were detected in the culture supernatant.

Example 10

Figure 6:
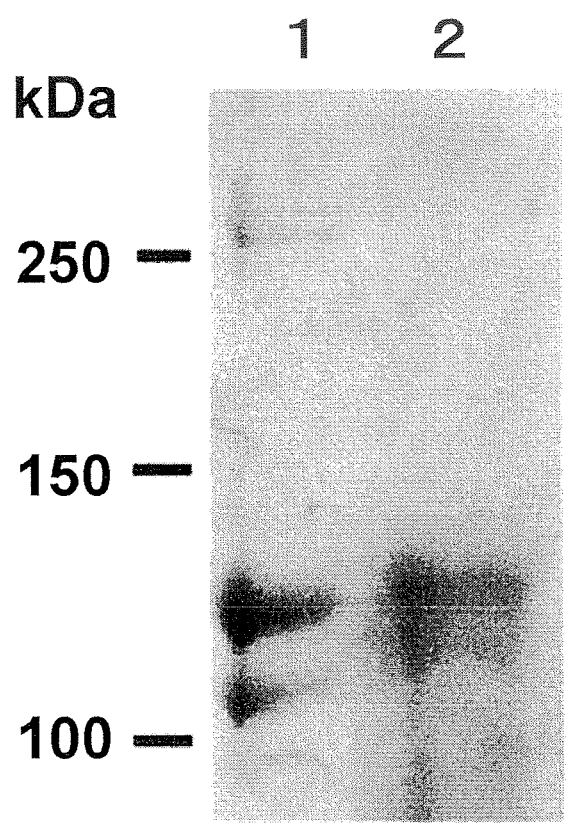
FIG. 6 is a photograph showing SDS-PAGE analysis of pepsin-digested products of recombinant human type I collagen in culture supernatants. Lane 1: recombinant human type I collagen (185 μg/mL), lane 2: recombinant human type I collagen (20 times concentrated).

Pepsin Digestion and SDS-PAGE Analysis of Recombinant Human Type I Collagen in the Culture Supernatant Pepsin digestion of the culture supernatant obtained from the human type I collagen-producing cell clone was carried out by adding 99.7% acetic acid to the supernatant at a final concentration of 0.5 M and then pepsin (Sigma Inc.) at a final concentration of 24 units/ml, followed by incubation at 20° C. for two hours. The pepsin digestion described below was carried out in the same way. The sample obtained from pepsin digestion was analyzed by SDS-polyacrylamide gel electrophoresis. 185 µg/mL of commercially available recombinant human type I collagen (Beckton, Dickinson and Company) was used as a comparative control. FIG. 6 shows the analytical result of the pepsin-digested products by SDS-polyacrylamide gel electrophoresis. As observed with the commercially available human type I atelocollagen, when treated with pepsin, the recombinant human type I collagen in the culture supernatant was detected as 130- and 120-kDa polypeptides, which may be α1 chain and α2 chain, respectively. These facts showed that recombinant human type I collagen that has a pepsin resistance substantially equivalent to that of the natural type was contained in the culture supernatant obtained from the human type I collagen-producing cell clone.

Example 11

Figure 7:
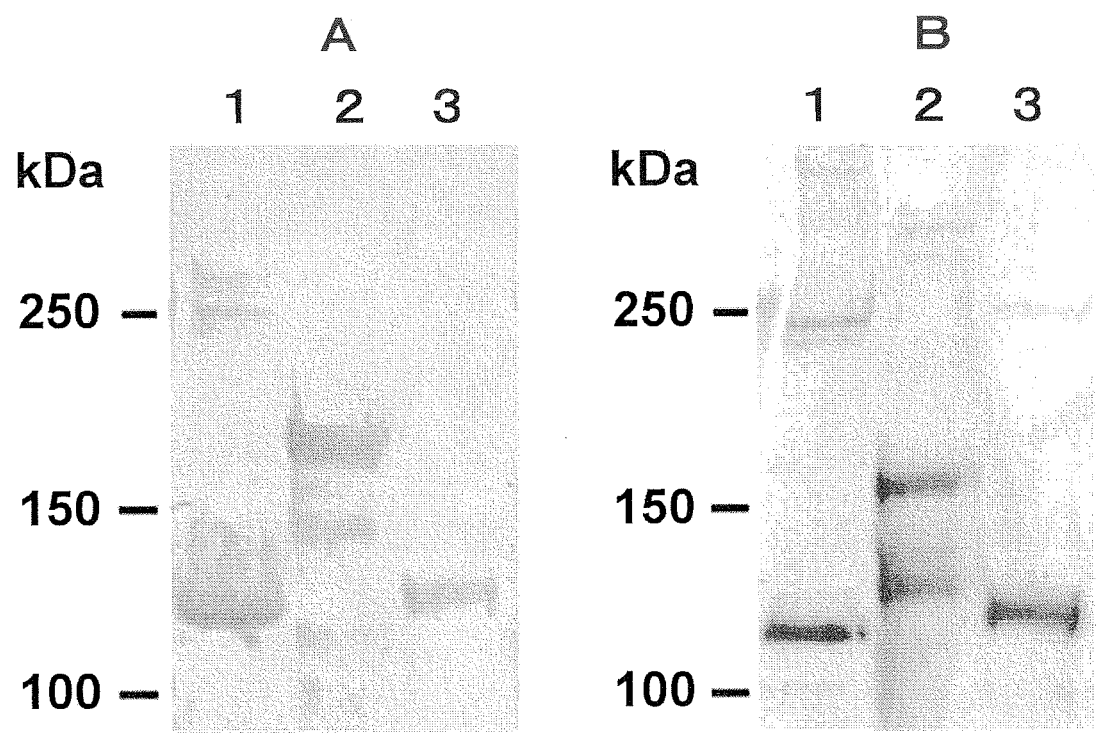
FIG. 7 is a set of photographs showing Western blot detection of purified recombinant human type I collagen and pepsin-digested products thereof.

Western Blot Analysis of the Recombinant Human Type I Collagen in the Culture Supernatant The polyacrylamide gel after SDS-polyacrylamide gel electrophoresis was immersed in a transfer buffer, and then human type I collagen in the polyacrylamide gel was transferred to a PVDF membrane by a conventional method. After blocking with Block Ace, the membrane was reacted with 2 µg/mL of an antibody against human type I collagen α1 chain and then with an anti-goat IgG antibody labeled with horseradish peroxidase (HRP). Reacted antibodies were detected by a method that uses the TMB peroxidase reagent for detecting HRP activity (Funakoshi Co.). 50 µg/mL of recombinant human type I collagen (Beckton, Dickinson and Company) was used as a comparative control. Human type I collagen α2 chain was detected using an antibody against human type I collagen α2 chain instead of an anti-human type I collagen α1 chain antibody. 10 µg/mL of human type I collagen was used as a comparative control. FIG. 7 shows the result of the Western blotting analysis. A 170 kDa polypeptide that may be a recombinant human type I collagen α1 chain which can be bound by an anti-human type I collagen α1 chain antibody, and 130- and 150-kDa polypeptides that may be recombinant human type I collagen α2 chains which can be bound by an anti-human type I collagen α2 chain antibody, were detected in the culture supernatant.

Example 12

Purification of Human Type I Collagen in the Culture Supernatant 100 mL of the Culture Supernatant Containing Human Type I Collagen was Purified as Follows The 100 ml culture supernatant filtrated through a 0.45 μm membrane filter (Millipore Co.) was concentrated to 30 mL by centrifugation at 3,000 rpm at 4° C. using a centrifugal concentration filter (VIVASPIN20 (MWCO 10,000): Sartorius).

Salting out was carried out by gradually adding 30 mL of 90% ammonium sulfate solution to the above concentrated culture supernatant while stirring at 4° C. After all the ammonium sulfate solution was added, the mixture was further stirred for an hour. Then, the mixture was allowed to stand on ice for one hour, and then centrifuged at 18,000 rpm, 4° C. for 30 minutes in a high-speed refrigerated centrifuge. Collagen in the solution was insolubilized by salting out and floated on the surface of the solution, and then collected and solubilized completely in 5 mL of D-PBS (Sigma Co.). This solution was filtrated through a 0.45 μm membrane filter (Millipore Co.), and then purified by gel filtration using Superose 6 (Amersham Biosciences) equilibrated with D-PBS, and the first peak was isolated. The collected peak fraction was concentrated about 20 times using VIVASPIN6 (MWCO 100,000). An appropriate amount of D-PBS was added to the concentrated collagen solution for further concentration, and low molecular fragments were removed. This D-PBS addition was repeated at least three times or more.

A purified collagen solution obtained from the original 100 mL culture supernatant was concentrated to approximately 300 μL and electrophoresed by SDS-PAGE to confirm its purity.

Example 13

Test of Human Type II Collagen Production: Transfer of the Human Type II Collagen Gene Using Expression Vector pNOW-hColIIa1 and Establishment of Primary G418-Resistant Clones One microgram of pNOW-hColIIa1 was transferred into 1.5 million CHO-DG44 cells in a 25 cm² culture flask using the lipofectin method. The transfer method was carried out according to the manufacturer's instructions. After 48 hours, the cells were removed by trypsin treatment and the number of cells was counted. $5 \times 10^5$ cells were diluted with 100 mL of Iscove's Modified Dulbecco's Medium containing 0.8 mg/mL G418 and 10% dialyzed fetal bovine serum, and then seeded into ten 96-well microtiter plates (960 wells), followed by culturing at 37° C. for three weeks under the presence of 5% carbon dioxide gas. Live cells in 126 wells were transferred to 24 well plates with 1 mL of Iscove's Modified Dulbecco's Medium containing 0.8 mg/mL G418 and 10% dialyzed fetal bovine serum, and were cultured until confluent. After culture supernatants were discarded, 1 mL PBS (Invitrogen Inc.) was added to each well, and culture supernatants were discarded again. 0.5 mL of ProCHO4 (Takara Bio Inc.), a serum-free CD medium for CHO cells, was added to each well and cultured at 37° C. for 96 hours under the presence of 5% carbon dioxide gas. Next, the amount of human type II collagen produced in the culture supernatants was examined.

Example 14

Quantitative Assay of the Human Type II Collagen Produced by pNOW-hColIIa1-Transduced Cell Clones The amount produced was assayed by SDS-polyacrylamide gel electrophoresis. 7.5 μL of the culture supernatant was mixed with an equal volume of Tris-SDSβ-ME sample treatment solution (Daiichi Pure Chemicals Co., Ltd.), and heat-treated at 95° C. for 5 minutes. This mixture was loaded onto an SDS-polyacrylamide gel (PAGEL, ATTO Inc.) and fractionated by electrophoresis. After the electrophoresis was finished, human type II collagen in the polyacrylamide gel was detected and quantified by treating the gel with Coomassie Brilliant Blue Staining Solution (Amersham Biosciences). 12.5 μg/mL to 100 μg/mL of human type II collagen (Cosmo Bio Co., Ltd.) treated in the same way was used as a comparative control.

Example 15

Gene Amplification in G418-Resistant Cell Lines

Among G418-resistant cell lines, a cell clone that produced the largest amount of human type II collagen was stabilized by passaging and culturing, and then gene amplification was carried out using MTX. Amplification was first carried out in a medium containing 5 nM MTX for one week, a medium containing 25 nM MTX for one week, a medium containing 50 nM MTX for one week, a medium containing 250 nM MTX for three weeks, and a medium containing 1 μM MTX for three weeks. As a result, the production level of human type II collagen increased to 70 μg/mL culture medium (four days) when MTX reached 25 nM. Generally, multiple MTX concentrations between 10 nM and 10 μM are used for gene amplification, and 10 μM is often used as a final concentration. However, exposure to high concentration is problematic when establishing stable recombinant cell lines because of cellular toxicity. Thus, it is also an important criterion that high productivity is achieved at low MTX concentrations, and thus concentrations up to 1 μM were used in the present experiment. Further, although the period of MTX exposure, including selection, is usually six to twelve months, the present experiment was done in about nine weeks. Despite these experimental conditions, the amount of human type II collagen produced was found to be effectively increased. Gene amplification in the G418-resistant cell lines described below was carried out in the same way.

Example 16

Analysis of Recombinant Human Type II Collagen in the Culture Supernatant by SDS-Polyacrylamide Gel Electrophoresis The cell clone massively producing human type II collagen obtained by gene amplification was adjusted to $1 \times 10^6$ cells/mL in a 25 cm² culture flask using the IS CHO-CD culture medium (IS Japan Co., Ltd.). After culturing at 37° C. for 96 hours under the presence of 5% carbon dioxide gas, the culture fluid was collected and the cells were removed by centrifugation to obtain a culture supernatant. 7.5 μL of the culture supernatant was mixed with an equal volume of Tris-SDSβ-ME sample treatment solution (Daiichi Pure Chemicals Co., Ltd.), and heat-treated at 95° C. for 5 minutes. This mixture was loaded onto an SDS-polyacrylamide gel (PAGEL, ATTO Inc.) and fractionated by electrophoresis. The SDS-polyacrylamide gel electrophoresis described below was carried out in the same way. After the electrophoresis was finished, human type II collagen in the polyacrylamide gel was detected by treating the gel with Coomassie Brilliant Blue Staining Solution (Amersham Biosciences). 100 μg/mL of human type II collagen (Cosmo Bio Co., Ltd.) treated in the same way was used as a comparative control. FIG. 8 shows the SDS-PAGE analysis result of the culture supernatant obtained from the human type II collagen-producing cell clone. 170- and 200-kDa polypeptides that may be recombinant human type II collagen were detected in the culture supernatant.

Example 17

Western Blot Analysis of Recombinant Human Type II Collagen in the Culture Supernatant The polyacrylamide gel after SDS-polyacrylamide gel electrophoresis was immersed in a transfer buffer, and then human type II collagen in the polyacrylamide gel was transferred to a PVDF membrane by a conventional method. After blocking with Block Ace, the membrane was reacted with 1 μg/mL of an antibody against the human type II collagen chain (Cosmo Bio Co., Ltd.), and then with an anti-rabbit IgG antibody labeled with horseradish peroxidase (HRP). Reacted antibodies were detected by a method of detecting HRP activity using the TMB peroxidase reagent (Funakoshi Co.). 10 μg/mL of human type II collagen (Cosmo Bio Co., Ltd.) was used as a comparative control. 170-kDa polypeptide which may be recombinant human type II collagen that can be bound by an antibody against the human type II collagen chain was detected in the culture supernatant (FIG. 9).

Example 18

Pepsin Digestion, SDS-Page Analysis, and Western Blot Analysis of Recombinant Human Type II Collagen in the Culture Supernatant A sample obtained from pepsin digestion was analyzed by SDS-polyacrylamide gel electrophoresis. 100 μg/mL of human type II collagen (Cosmo Bio Co., Ltd.) was used as a comparative control. FIG. 10 shows the result of analyzing the pepsin-digested products by SDS-polyacrylamide gel electrophoresis. As observed with commercially available human type II atelocollagen, when treated with pepsin, the recombinant human type II collagen in the culture supernatant was detected as a polypeptide of 130 kDa. These facts showed that recombinant human type II collagen that has a pepsin resistance substantially equivalent to that of the natural type collagen was contained in the culture supernatant obtained from the human type II collagen-producing cell clone. The same results were obtained by Western blot analysis (FIG. 11).

Example 19

Test of Human Type III Collagen Production: Transfer of Human Type III Collagen Gene Using Expression Vector pNOW-hColIIIa1 and Establishment of Primary G418-Resistant Clones One microgram of pNOW-hColIIIa1 was transferred into 1.5 million CHO DG44 cells in a 25 $cm^2$ culture flask by the lipofectin method. The transfer method was carried out according to the manufacturer's instructions. After 48 hours, the cells were removed by trypsin treatment, and the number of cells was counted. Then, $3 \times 10^3$ cells were diluted with 100 mL of Iscove's Modified Dulbecco's Medium containing 0.8 mg/mL G418 and 10% dialyzed fetal bovine serum, and seeded in ten 96-well microtiter plates (960 wells), followed by culturing at 37° C. under the presence of 5% carbon dioxide gas for three weeks. As a result, live cells were found only in 117 wells (G418 resistant). The live cells were transferred to 24 well plates with 1 mL of Iscove's Modified Dulbecco's Medium containing 0.8 mg/mL G418 and 10% dialyzed fetal bovine serum, and cultured until confluent. After culture supernatants were discarded, 1 mL of PBS (Invitrogen Inc.) was added to each well, and culture supernatants were discarded again. 0.5 mL of CHO-S-SFM II (Invitrogen Inc.), a serum-free medium for CHO cells, was added to each well and cultured at 37° C. for 72 hours under the presence of 5% carbon dioxide gas. Subsequently, the amount of human type III collagen produced in the culture supernatants was examined.

Example 20

Quantitative Assay of the Human Type III Collagen Produced in pNOW-hColIIIa1-Transduced Cell Clones The amount produced was assayed by a dot blotting method. A nylon membrane was dotted with 1 μL of 72-hour culture supernatant, 1 μL each of commercially available human type III collagen (Beckton, Dickinson and Company) 2× diluted (0.125 to 8 μg/mL) in a serum-free medium for CHO cells, CHO-S-SFM II, and 1 μL of CHO-S-SFM II alone; and was then air dried for one hour. After blocking with Block Ace, the membrane was reacted with 1 μg/mL of an anti-human type III collagen antibody (Cosmo Bio Co., Ltd.) and then with an HRP-labeled anti-rabbit IgG antibody. Reacted antibodies were detected by a method of detecting HRP activity with the SuperSignal West Pico reagent using Lumino Capture.

Example 21

Gene Amplification in G418-Resistant Cell Lines

Among G418-resistant cell lines, a cell clone that produced the largest amount of human type III collagen was stabilized by passaging and culturing, and then gene amplification was carried out with MTX. Gene amplification was carried out first in a medium containing 15 nM MTX for two weeks, a medium containing 60 nM MTX for two weeks, a medium containing 250 nM MTX for two weeks, and a medium containing 1 μg/mL MTX for four weeks. As a result, the production level of human type III collagen was increased to 225 μg/mL culture medium (three days).

Example 22

SDS-PAGE Analysis of Recombinant Human Type III Collagen in the Culture Supernatant The cell clone massively producing human type III collagen obtained by gene amplification was adjusted to $1\times10^6$ cells/mL in a 25 cm² culture flask by using the IS CHO-CD culture medium (IS Japan Co., Ltd.). After culturing at 37° C. for 96 hours under the presence of 5% carbon dioxide gas, the culture fluid was collected and the cells were removed by centrifugation to obtain a culture supernatant. 6.0 µL of the culture supernatant was mixed with an equal volume of Tris-SDSβ-ME sample treatment solution (Daiichi Pure Chemicals Co., Ltd.), and heat-treated at 95° C. for 5 minutes. This mixture was loaded onto an SDS-polyacrylamide gel (PA-GEL, ATTO Inc.) and fractionated by electrophoresis. The SDS-polyacrylamide gel electrophoresis described below was carried out in the same way. After the electrophoresis was finished, human type III collagen in the polyacrylamide gel was detected by treating the gel with Coomassie Brilliant Blue Staining Solution (Amersham Biosciences). 100 µg/mL of human type III collagen (Beckton, Dickinson and Company) treated in the same way was used as a comparative control. FIG. 12 shows the result of SDS-PAGE analysis of the culture supernatant obtained from the human type III collagen-producing cell clone. 140- and 170-kDa polypeptides that may be recombinant human type III collagen were detected in the culture supernatant.

Example 23

Western Blot Analysis of Recombinant Human Type III Collagen in the Culture Supernatant The polyacrylamide gel after SDS-polyacrylamide gel electrophoresis was immersed in a transfer buffer, and then human type III collagen in the polyacrylamide gel was transferred to a PVDF membrane by a conventional method. After blocking with Block Ace, the membrane was reacted with 1 µg/mL of an antibody against the human type III collagen chain (Cosmo Bio Co., Ltd.), and then with an anti-rabbit IgG antibody labeled with horseradish peroxidase (HRP). Reacted antibodies were detected by a method of detecting HRP activity using the TMB peroxidase reagent (Funakoshi Co.). 100 µg/mL of human type III collagen (Beckton, Dickinson and Company) was used as a comparative control. 140- and 170-kDa polypeptides that may be recombinant human type III collagen which can be bound by an antibody against the human type III collagen chain were detected in the culture supernatant (FIG. 13).

As observed with commercially available human type III atelocollagen (Beckton, Dickinson and Company), when treated with pepsin, the recombinant human type III collagen in the supernatant was detected as a polypeptide at 130 kDa. These facts showed that recombinant human type III collagen that has a pepsin resistance substantially equivalent to that of the natural type was contained in the culture supernatant obtained from the human type III collagen-producing cell clone.

Example 24

Purification of Human Type I and Type III Collagens in the Culture Supernatants Purification was carried out using 100 mL of the culture supernatant containing human type I or type III collagen in Example 12. A purified collagen solution obtained from the original 100 mL culture supernatant was concentrated to approximately 300 µL and electrophoresed by SDS-PAGE to confirm its purity. (FIG. 14).

INDUSTRIAL APPLICABILITY

The present invention can provide expression vectors and human collagen-producing cells that enable production of recombinant human collagen that has high quality and is closer to the natural type. The invention can also provide cells that produce triple-helix structure human collagen.

The production methods of the present invention can be applied not only to collagen but also to proteins that have a triple-helix structure, such as collectin.

Furthermore, the collagen production method of the present invention may be used to produce large quantities of triple-helix structural collagen with a novel molecular composition, which cannot be produced (or has not been discovered) in nature, by simultaneously expressing different types of α chains. Triple-helix structure collagen with a novel molecular composition may have properties that are different from those of known collagen, and is therefore expected to be applied as a new material.

The invention claimed is:

1. A method of producing a protein having a triple-helix structure, wherein the method comprises:
   (a) introducing DNA encoding a protein having a triple-helix structure into a pNOW/CMV-AA vector;
   (b) transforming an isolated cell with the vector, wherein the isolated cell is a Chinese hamster ovary (CHO) cell to thereby provide a transformed cell; and
   (c) culturing or breeding the transformed cell, and
   (d) collecting a protein having a triple helix structure from the transformed cell or culture supernatant thereof, thereby obtaining an expression level of 50 μg/mL or more of the protein having a triple helix structure is selected from the group consisting of human type I collagen, human type II collagen, and human type III collagen or a partial peptide thereof.

2. The method of claim 1, wherein the human collagen consists of at least one or more types of α chains.

3. The method of claim 1, wherein the human collagen is human type I collagen.

4. The method of claim 1, wherein the human type I collagen is a complex of α1 and α2 chains.

5. The method of claim 1, wherein the human collagen is human type II collagen.

6. The method of claim 1, wherein the human collagen is human type III collagen.

7. The method of claim 1, wherein the DNA encoding a protein having a triple helix structure is at least a DNA selected from:
   (a) a DNA selected from the group consisting of:
      (A) both SEQ ID NOs: 1 and 4;
      (B) SEQ ID NO: 7; and
      (C) SEQ ID NO: 10; and
   (b) a DNA hybridizing under conditions of 42° C., 2×SSC, and 0.1% SDS, conditions of 50° C., 2×SSC, and 0.1% SDS, or conditions of 65° C., 0.1×SSC, and 0.1% SDS with a DNA selected from the group consisting of:
      (A) both SEQ ID NOs: 1 and 4;
      (B) SEQ ID NO: 7; and
      (C) SEQ ID NO: 10.

8. A pNOW/CMV-AA vector introduced with at least one DNA selected from a DNA comprising any one of the nucleotide sequences of SEQ ID NOs: 1, 4, 7, and 10.

9. A Chinese hamster ovary (CHO) cell carrying a pNOW/CMV-AA vector introduced with at least one DNA selected from:
(a) a DNA comprising any one of the nucleotide sequences of SEQ ID NOs: 1, 4, 7, and 10; and
(b) a DNA hybridizing under conditions of 42° C., 2×SSC, and 0.1% SDS, conditions of 50° C., 2×SSC, and 0.1% SDS, or conditions of 65° C., 0.1×SSC, and 0.1% SDS with DNA comprising any one of the nucleotide sequences of SEQ ID NOs: 1, 4, 7, and 10.

10. A kit for producing a protein having a triple helix structure, wherein the kit comprises the vector of claim 8 or the Chinese hamster ovary (CHO) cell of claim 9.

11. A method of producing a protein having a triple-helix structure, wherein the method comprises:
(a) introducing DNA encoding a protein having a triple-helix structure into a pNOW/CMV-AA vector;
(b) transforming an isolated cell with the vector, wherein the isolated cell is a Chinese hamster ovary (CHO) cell to thereby provide a transformed cell; and
(c) culturing or breeding the transformed cell:
(d) obtaining an expression level of 50 µg/mL or more of a protein having a triple helix structure; and
(e) collecting the protein having a triple helix structure from the transformed cell or culture supernatant thereof, wherein the DNA encoding a protein comprises:
a DNA hybridizing under conditions of 42° C., 2×SSC, and 0.1% SDS, conditions of 50° C., 2×SSC, and 0.1% SDS, or conditions of 65° C., 0.1×SSC, and 0.1% SDS with a DNA selected from the group consisting of:
(A) both SEQ ID NOs: 1 and 4;
(B) SEQ ID NO: 7; and
(C) SEQ ID NO: 10.

* * * * *